United States Patent [19]
Borden et al.

[11] Patent Number: 5,824,486
[45] Date of Patent: Oct. 20, 1998

[54] GLYCINE TRANSPORTER-TRANSFECTED CELLS AND USES THEREOF

[75] Inventors: Laurence A. Borden, Hackensack, N.J.; Michael De Vivo, New York, N.Y.; Midori Yokoyama, Highland Park; Vivian R. Albert, Montclair, both of N.J.

[73] Assignee: Allelix Neuroscience Inc., South Plainfield, N.J.

[21] Appl. No.: 655,836

[22] Filed: May 31, 1996

[51] Int. Cl.$^6$ .................................................. G01N 33/567
[52] U.S. Cl. .................... 435/72; 435/7.1; 435/252.3; 435/320.1; 435/325; 536/23.1; 536/23.5; 530/350
[58] Field of Search ................... 485/7.1, 7.2, 252.3, 485/320.1; 536/23.1, 23.5; 530/350

[56] References Cited

PUBLICATIONS

Kanner and Schuldiner, *CRC Critical Reviews In Biochemistry*, 22, pp. 1032 et seq. (1987).
Attwell et al., *Neuron*, 11, pp. 401–407 (1993).
Johnson and Ascher, *Nature*, 325, pp. 529–531 (1987).
Fletcher et al., *Glycine Transmission*, (Otterson and Storm-Mathisen, eds.) pp. 193–219 (1990).
Smith et al., *Neuron*, 8, pp. 927–935 (1992).
Liu et al., *J. Biological Chemistry*, 268, pp. 22802–22808 (1993).
Jursky and Nelson, *J. Neurochemistry*, 64, pp. 1026–1033 (1995).
Uhl, *Trends In Neuroscience*, 15, pp. 265–268 (1992).
Clark and Amara, *BioEssays*, 15, pp. 323–332 (1993).
Yaksh, *Pain*, pp. 111–123 (1989).
Troung et al., *Movement Disorders*, 3, pp. 77–87 (1988).
Becker, *FASEB J.*, 4, pp. 2767–2774 (1990).
Rison and Stanton, *Neurosci. Biobehav. Rev.*, 19, pp. 533–552 (1995).
Danysz et al., *Behaviorial Pharmacol.*, 6, pp. 455–474 (1995).
Olney and Farber, *Archives General Psychiatry*, 52, pp. 998–1007 (1996).
Coyle and Puttfarcken, *Science*, 262, pp. 689–695 (1993).
Lipton and Rosenberg, *New Engl. J. of Medicine*, 330, pp. 613–622 (1993).
Choi, *Neuron*, 1, pp. 623–634 (1988).
Pitkanen et al., *Eur. J. Pharmacol.*, 253, pp. 125–129 (1994).
Thiels et al., *Neuroscience*, 46, pp. 501–509 (1992).
Kretschmer and Schmidt, *J. Neurosci.*, 16, pp. 1561–1569 (1996).
Grimwood et al., *Molecular Pharmacol.*, 49, pp. 923–930 (1992).
Sterner and Calligro, *Soc. Neurosci. Abstr.*, 49, p. 351 (1995).
Calligaro et al., *J. Neurochem.*, 60, pp. 2297–2303 (1993).
Brennan, *Chem. Eng. News*, pp. 41–47, (May 13, 1996).
Leeson, *Drug Design For Neuroscience*, (Alan P. Kozikowski, ed., 1993) pp. 339–383.
Yoneda et al., *Neurochem.*, 62, pp. 102–112 (1994).
Yoneda et al., *J. Neurochem.*, 60, pp. 634–645 (1993).
Palmer and Burns, *J. Neurochem.*, 62, pp. 187–196 (1994).
Lu et al., *Proc. Natl. Acad. Sci. USA*, 88, pp. 6289–6292 (1991).
Kim et al. (1994) Molec. Pharm. 45: 608–617.
Blakely et al. (1988) PNAS 85: 9846–9850.
Shimada et al. (1991) Science 254:576–578.
Lipsick et al. (1986) J. Vir. 59: 267–275.

*Primary Examiner*—Stephen Walsh
*Assistant Examiner*—Kenneth A. Sorensen
*Attorney, Agent, or Firm*—Dechert Price & Rhoads

[57] ABSTRACT

The present invention relates to materials and methods for the identification of agents that regulate glycine transport in or out of cells, particularly in or out of neuronal and neuronal-associated cells. Such materials include non-mammalian cells having transfected therein a glycine transporter. The methods relate to the manipulation of such cells such that agents are identified that cause intake or outflow of glycine with respect to a given glycine transporter.

16 Claims, 3 Drawing Sheets

GLYCINE TRANSPORTER-TRANSFECTED CELLS AND USES THEREOF

The present invention relates to the field of drug discovery, particularly with respect to drugs that have an effect on glycine-mediated neurotransmission in the nervous system.

Synaptic transmission is a complex form of intercellular communication that involves a considerable array of specialized structures in both the pre- and post-synaptic neuron. High-affinity neurotransmitter transporters are one such component, located on the pre-synaptic terminal and surrounding glial cells (Kanner and Schuldiner, *CRC Critical Reviews in Biochemistry*, 22, 1032 (1987)). Transporters sequester neurotransmitter from the synapse, thereby regulating the concentration of neurotransmitter in the synapse, as well as its duration therein, which together influence the magnitude of synaptic transmission. Further, by preventing the spread of transmitter to neighboring synapses, transporters maintain the fidelity of synaptic transmission. Last, by sequestering released transmitter into the presynaptic terminal, transporters allow for transmitter reutilization.

Neurotransmitter transport is dependent on extracellular sodium and the voltage difference across the membrane; under conditions of intense neuronal firing, as, for example, during a seizure, transporters can function in reverse, releasing neurotransmitter in a calcium-independent non-exocytotic manner (Attwell et al., *Neuron*, 11, 401–407 (1993)). Pharmacologic modulation of neurotransmitter transporters thus provides a means for modifying synaptic activity, which provides useful therapy for the treatment of neurological and psychiatric disturbances.

The amino acid glycine is a major neurotransmitter in the mammalian nervous system, functioning at both inhibitory and excitatory synapses. By nervous system, both the central and peripheral portions of the nervous system are intended. These distinct functions of glycine are mediated by two different types of receptor, each of which is associated with a different class of glycine transporter. The inhibitory actions of glycine are mediated by glycine receptors that are sensitive to the convulsant alkaloid, strychnine, and are thus referred to as "strychnine-sensitive." Such receptors contain an intrinsic chloride channel that is opened upon binding of glycine to the receptor; by increasing chloride conductance, the threshold for firing of an action potential is increased. Strychnine-sensitive glycine receptors are found predominantly in the spinal cord and brainstem, and pharmacological agents that enhance the activation of such receptors will thus increase inhibitory neurotransmission in these regions.

Glycine functions in excitatory transmission by modulating the actions of glutamate, the major excitatory neurotransmitter in the central nervous system. See Johnson and Ascher, *Nature*, 325, 529–531 (1987); Fletcher et al., *Glycine Transmission*, (Otterson and Storm-Mathisen, eds., 1990), pp. 193–219. Specifically, glycine is an obligatory co-agonist at the class of glutamate receptor termed N-methyl-D-aspartate (NMDA) receptor. Activation of NMDA receptors increases sodium and calcium conductance, which depolarizes the neuron, thereby increasing the likelihood that it will fire an action potential. NMDA receptors are widely distributed throughout the brain, with a particularly high density in the cerebral cortex and hippocampal formation.

Molecular cloning has revealed the existence in mammalian brains of two classes of glycine transporters, termed GlyT-1 and GlyT-2. GlyT-1 is found predominantly in the forebrain, and its distribution corresponds to that of glutamatergic pathways and NMDA receptors (Smith, et al., *Neuron*, 8, 927–935 (1992)). Molecular cloning has further revealed the existence of three variants of GlyT-1, termed GlyT-1a, GlyT-1b and GlyT-1c (Kim et al., *Molecular Pharmacology*, 45, 608–617 (1994)), each of which displays a unique distribution in the brain and peripheral tissues. These variants arise by differential splicing and exon usage, and differ in their N-terminal regions. GlyT-2, in contrast, is found predominantly in the brain stem and spinal cord, and its distribution corresponds closely to that of strychnine-sensitive glycine receptors (Liu et al., *J. Biological Chemistry*, 268, 22802–22808 (1993); Jursky and Nelson, *J. Neurochemistry*, 64, 1026–1033 (1995)). These data are consistent with the view that, by regulating the synaptic levels of glycine, GlyT-1 and GlyT-2 selectively influence the activity of NMDA receptors and strychnine-sensitive glycine receptors, respectively.

Sequence comparisons of GlyT-1 and GlyT-2 have revealed that these glycine transporters are members of a broader family of sodium-dependent neurotransmitter transporters, including, for example, transporters specific for γ-amino-n-butyric acid (GABA) and others. Uhl, *Trends in Neuroscience*, 15, 265–268 (1992); Clark and Amara, *BioEssays*, 15, 323–332 (1993). Overall, each of these transporters includes 12 putative transmembrane domains that predominantly contain hydrophobic amino acids. Comparing rat GlyT-1a or rat GlyT-1b to rat GlyT-2, using the Lipman-Pearson FASTA algorithm, reveals a 51% amino acid sequence identity and a 55% nucleic acid sequence identity. Comparison of the sequence of human GlyT-1a, human GlyT-1b, or human GlyT-1c with rat GlyT-2 reveals in each case a 51% amino acid sequence identity and a 53–55% nucleic acid sequence identity. However, there are segments of human GlyT-1c 16 amino acids in length whose amino acid sequences are 100% identical to those of rat GlyT-2; the corresponding nucleic acid sequence of this region, which is 48 nucleotides in length, is 78–85% identical between the two transporters. A yet longer stretch of approximately 260 amino acids displays 53% amino acid sequence identity between human GlyT-1c and rat GlyT-2; the corresponding nucleotide sequence for this region, 780 nucleotides in length, displays about 66% sequence identity between the two transporters.

Compounds that inhibit or activate glycine transporters would be expected to alter receptor function, and provide therapeutic benefits in a variety of disease states. For example, inhibition of GlyT-2 can be used to diminish the activity of neurons having strychnine-sensitive glycine receptors via increasing synaptic levels of glycine, thus diminishing the transmission of pain-related (ie., nociceptive) information in the spinal cord, which has been shown to be mediated by these receptors. Yaksh, *Pain*, 111–123 (1989). Additionally, enhancing inhibitory glycinergic transmission through strychnine-sensitive glycine receptors in the spinal cord can be used to decrease muscle hyperactivity, which is useful in treating diseases or conditions associated with increased muscle contraction, such as spasticity, myoclonus, and epilepsy (Truong et al., *Movement Disorders*, 3, 77–87 (1988); Becker, *FASEB J.*, 4, 2767–2774 (1990)). Spasticity that can be treated via modulation of glycine receptors is associated with epilepsy, stroke, head trauma, multiple sclerosis, spinal cord injury, dystonia, and other conditions of illness and injury of the nervous system.

NMDA receptors are critically involved in memory and learning (Rison and Stanton, *Neurosci. Biobehav. Rev.*, 19, 533–552 (1995); Danysz et al., *Behavioral Pharmacol.*, 6, 455–474 (1995)); and, furthermore, decreased function of NMDA-mediated neurotransmission appears to underlie, or contribute to, the symptoms of schizophrenia (Olney and Farber, *Archives General Psychiatry,* 52, 998–1007 (1996)). Thus, agents that inhibit GlyT-1 and thereby increase glycine activation of NMDA receptors can be used as novel antipsychotics and anti-dementia agents, and to treat other diseases in which cognitive processes are impaired, such as attention deficit disorders and organic brain syndromes. Conversely, over-activation of NMDA receptors has been implicated in a number of disease states, in particular the neuronal death associated with stroke and possibly neurodegenerative diseases, such as Alzheimer's disease, multi-infarct dementia, AIDS dementia, Parkinson's disease, Huntington's disease, amyotrophic lateral sclerosis or other conditions in which neuronal cell death occurs, such as stroke and head trauma. Coyle & Puttfarcken, *Science,* 262, 689–695 (1993); Lipton and Rosenberg, *New Engl. J. of Medicine,* 330, 613–622 (1993); Choi, *Neuron,* 1, 623–634 (1988). Thus, pharmacological agents that increase the activity of GlyT-1 will result in decreased glycine-activation of NMDA receptors, which activity can be used to treat these, and related, disease states. Similarly, drugs that directly block the glycine site on the NMDA receptors can be used to treat these and related disease states.

Methods and materials are needed to identify the aforementioned pharmacological agents. In particular, a drug screening method or methods relating to the identification of pharmacological agents that regulate glycine transport or interact with glycine receptors are needed.

BRIEF SUMMARY OF THE INVENTION

The present invention relates to materials and methods for the identification of agents that regulate glycine transport in or out of cells, or that interact with glycine receptors. Such materials include cells having transfected therein a glycine transporter. The methods relate to the manipulation of such cells such that agents are identified that inhibit or stimulate intake or outflow of glycine with respect to a given glycine transporter.

In a preferred embodiment, the present invention relates to a non-mammalian cell comprising an exogenous nucleic acid encoding a glycine transporter. Such an embodiment allows for the specific demonstration of the activity of a mammalian transporter in a genetically different background. A non-mammalian cell of the present invention is selected from the group consisting of avian, fungal, insect, and reptilian; most preferably the cell is avian. Preferably, the exogenous nucleic acid of the present invention is mammalian; more preferably the exogenous nucleic acid is human or rat. As noted, the inventive non-mammalian cell includes the glycine transporter, which is glycine transporter-1 (GlyT-1) or glycine transporter-2 (GlyT-2), wherein GlyT-1 is GlyT-1a, GlyT-1b, or GlyT-1 c. Preferably, the glycine transporter is GlyT-1, wherein the exogenous nucleic acid is selected from the group consisting of SEQ ID NO:1, SEQ ID NO:2, and SEQ ID NO:3. In another embodiment, the glycine transporter is GlyT-2, wherein the exogenous nucleic acid is SEQ ID NO:4. The non-mammalian cell of the present invention preferably is a quail fibroblast, and most preferably is a QT-6 cell.

Another preferred embodiment of the present invention relates to a method for the analysis or screening of an agent for treatment of pain, muscle hyperactivity, neuronal cell death, schizophrenia, memory or cognitive disorders, or other disorders or conditions associated with a nervous system disorder or condition, comprising culturing separately first and second non-mammalian cells, wherein the first and second non-mammalian cells are of the same strain and comprise an exogenous nucleic acid encoding a glycine transporter, contacting the first non-mammalian cell with the agent, and screening for the enhancement or inhibition of glycine transport into the first non-mammalian cell as compared to glycine transport into the second non-mammalian cell that was not contacted with the compound. The nervous system disorder or condition noted hereinabove is selected from the group consisting of spasticity, muscle spasm, myoclonus, epilepsy, stroke, head trauma, multiple sclerosis, spinal cord injury, dystonia, Alzheimer's disease, multi-infarct dementia, AIDS dementia, Parkinson's disease, Huntington's disease, and amyotrophic lateral sclerosis. Preferably, the glycine transporter used in the context of this method is GlyT-1 or GlyT-2, wherein GlyT-1 is GlyT-1a, GlyT-1b, or GlyT-1c. A further preferred embodiment of the present invention includes first and second non-mammalian cells comprising exogenous nucleic acid that encodes GlyT-1, such as exogenous nucleic acid that comprises SEQ ID NO:1, SEQ ID NO:2, or SEQ ID NO:3. Alternatively, the first and second non-mammalian cells of the present invention includes exogenous nucleic acid that encodes GlyT-2, such as exogenous nucleic acid that comprises SEQ ID NO:4. In a preferred embodiment, the non-mammalian cell of the present invention is a QT-6 cell. In yet a further preferred embodiment, the drug discovered by the inventive method is an enhancer or inhibitor of GlyT-1 or GlyT-2 or both GlyT-1 and GlyT-2.

DETAILED DESCRIPTION

Figures 1A, 1B:
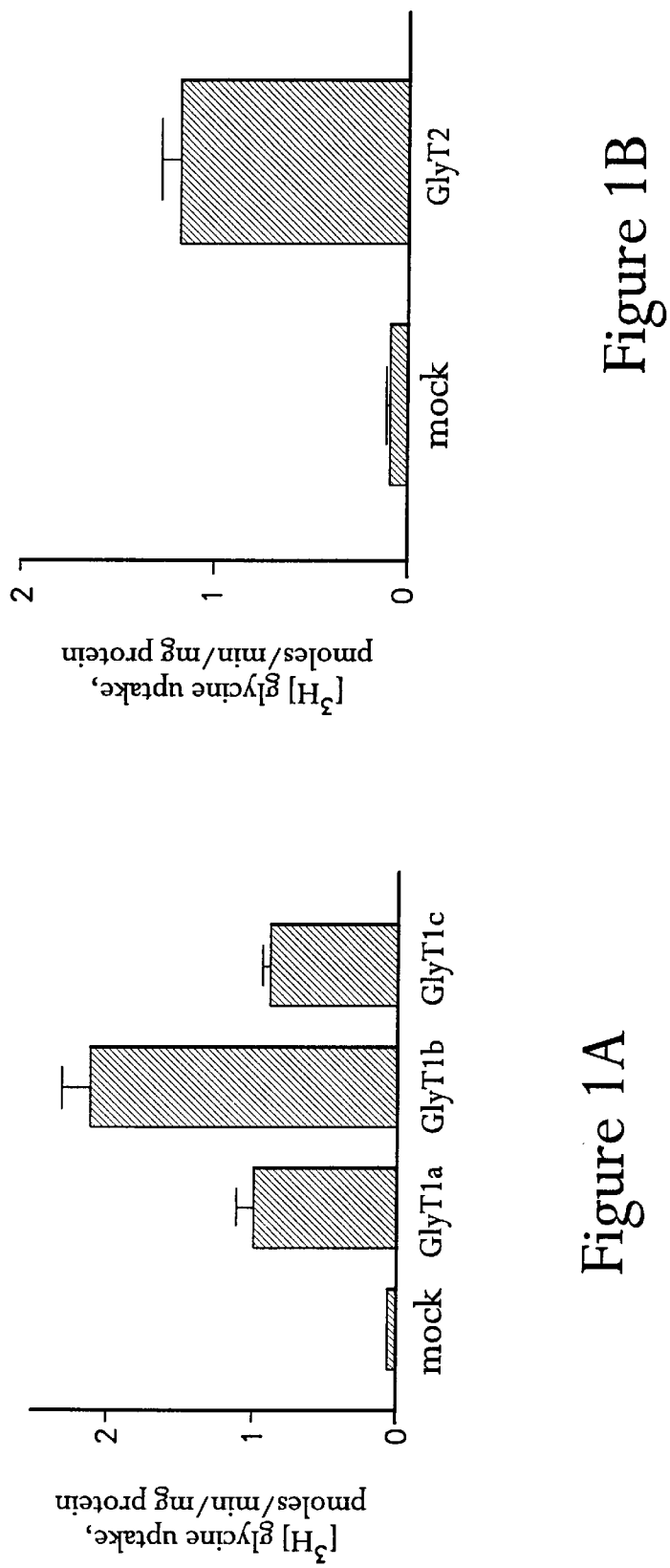
FIGS. 1A and 1B are bar graphs that depict the results of heterologous expression of glycine transporters in QT-6 cells.

The present invention is directed to materials and methods for the identification of agents that regulate glycine transport in or out of cells or that interact with glycine receptors. In particular, such glycine transport is mediated or caused by action of the glycine transporter type 1 (GfyT-1) or glycine transporter type 2 (GlyT-2). GlyT-1 has been found to express as three different isoforms that differ in their 5' ends; namely, GlyT-1a [SEQ ID NO:1], GlyT-1b [SEQ ID NO:2], and GlyT-1c [SEQ ID NO:3]. GlyT-1a is transcribed from a different promoter than is GlyT-1b and GlyT-1c; all three isoforms differ by differential splicing and exon usage. Adams et al., *J. Neurosci.,* 15, 2524–2532 (1995); Kim et al., *Molec. Pharmacol.* 45, 608–617 (1994).

The glycine transporter genes and their respective gene products are responsible for the reuptake of glycine from the synaptic cleft into presynaptic nerve endings or glial cells, thus terminating the action of glycine. Neurological disorders or conditions associated with improperly controlled glycine receptor activity, or which could be treated with therapeutic agents that modulate glycine receptor activity, include spasticity (Becker, *FASEB Journal,* 4, 2767–2774 (1990)) and pain realization (Yaksh, *Pain,* 37, 111–123 (1989)). Additionally, glycine interacts at N-methyl-D- aspartate (NMDA) receptors, which have been implicated in learning and memory disorders and certain clinical conditions such as epilepsy, Alzheimer's and other cognition-related diseases, and schizophrenia. See Rison and Stanton, *Neurosci. Biobehav. Rev.*, 19, 533–552 (1995); Danysz et al., *Behavioral Pharmacol.*, 6, 455–474 (1995).

Compounds that inhibit GlyT-1 mediated glycine transport will increase glycine concentrations at NMDA receptors, which receptors are located in the forebrain, among other locations. This concentration increase elevates the activity of NMDA receptors, thereby alleviating schizophrenia and enhancing cognitive function. Alternatively, compounds that interact directly with the glycine receptor component of the NMDA receptor can have the same or similar effects as increasing or decreasing the availability of extracellular glycine caused by inhibiting or enhancing GlyT-1 activity, respectively. See, for example, Pitkänen et al., *Eur. J. Pharmacol.*, 253, 125–129 (1994); Thiels et al., *Neuroscience*, 46, 501–509 (1992); and Kretschmer and Schmidt, *J. Neurosci.*, 16, 1561–1569 (1996). Compounds that inhibit GlyT-2 mediated glycine transport will increase glycine concentrations at receptors located primarily in the brain stem and spinal cord, where glycine acts as an inhibitor of synaptic transmission. These compounds are effective against epilepsy, pain and spasticity, and other such conditions. See, for example, Becker, supra, and Yaksh, supra.

Accordingly, the identification of agents that enhance or inhibit the glycine transporter, or inhibit or activate the glycine receptor portion of the NMDA receptor, is important for the development of drugs useful in the treatment of such neurological conditions and disorders. The present invention provides materials and methods that are suitable for such screening. In particular, GlyT-1a, -1b, -1c, and GlyT-2 DNA sequences, when placed into a suitable expression vector and a suitable host is transformed therewith, the GlyT-1a, -1b, -1c, and GlyT-2, respectively, glycine transporter polypeptides are synthesized and form the respective glycine transporter. Such transformed cells may form stable lines that constitutively or inductively express the GlyT DNA, thus expressing glycine transporters. Alternatively, other such cells may exhibit transient expression of the GlyT DNA and protein. Either of such transfected cells, together or separately, are useful for screening assays to determine whether a candidate agent has characteristics of enhancing or inhibiting glycine transport, as disclosed herein with respect to the present invention. Additionally, suitable primary neuronal cell cultures that have NMDA receptors and glycine transporters are also used in the context of the present invention to test compounds for the ability to activate or inhibit either the glycine transporter, the glycine receptor portion of the NMDA receptor, or both. Such tests also have the form of binding assays using membranes from any suitable source that includes NMDA receptors, such as brain tissue.

Suitable expression vectors include pRc/CMV (Invitrogen), pRc/RSV (Invitrogen), pcDNA3 (Invitrogen), Zap Express Vector (Stratagene Cloning Systems, LaJolla, CA; hereinafter "Stratagene"), pBk/CMV or pBk-RSV vectors (Stratagene), Bluescript ll SK±Phagemid Vectors (Stratagene), LacSwitch (Stratagene), pMAM and pMAM neo (Clontech), among others. A suitable expression vector is capable of fostering expression of the included GlyT DNA in a suitable host cell, preferably a non-mammalian host cell, which can be eukaryotic, fungal, or prokaryotic. Such preferred host cells include, but are not limited to, avian, fungal, insect, and reptilian cells. Preferred host cells are avian, fungal, and insect cells. Most preferred host cells are avian cells. Preferred avian cells include those of quails, chickens, and turkeys; more preferred, of quails. Most preferred of such cells are quail fibroblast, such as, in particular, QT-6.

The GlyT DNA that is inserted into one of the aforementioned expression vectors is any suitable DNA that encodes a glycine transporter. Preferably, the GlyT DNA is obtained from a suitable animal, including but not limited to birds and mammals, for example. Preferred mammals include humans, mice, rats, cows, pigs, among others; more preferably, the GlyT DNA is obtained from a human or a rat; most preferably, the GlyT DNA is obtained from a human. In one embodiment, the GlyT DNA is preferably comprised of SEQ ID NO:1, SEQ ID NO:2, or SEQ ID NO:3, with respect to GlyT-1, and SEQ ID NO:4, with respect to GlyT-2. Any other suitable DNA that encodes glycine transporter type 1 activity is an equivalent substitution for SEQ ID Nos:1–3. Similarly, any other suitable DNA that encodes glycine transporter type 2 activity is an equivalent substitution for SEQ ID NO:4.

In another embodiment, the GlyT DNA used in the context of the present invention encodes a protein that has at least about 45% amino acid sequence identity with at least one of the proteins encoded by SEQ ID NOs:1–4, more preferably at least about 60% amino acid sequence identity, still more preferably at least about 75% amino acid sequence identity, yet still more preferably at least about 85% amino acid sequence identity. Sequence identity measurements as contemplated herein score conservative amino acid substitutions as identical, wherein conservative substitutions are those that cause exchanges of amino acids in the encoded protein, which amino acids have highly similar physico-chemical characteristics or have been known empirically to substitute in homologous proteins. At the nucleic acid level, exchanges of nucleotides can occur that are neutral in their effect on the encoded protein sequence, in consequence of the redundancy of the genetic code, which could account for greater sequence variation at the nucleic acid level than at the amino acid level.

Such exchangeable amino acids are categorized within one of the following groups, wherein the amino acids are recited by their respective three-letter codes that are well known in the art:

1. Small aliphatic, nonpolar or slightly polar residues: Ala, Ser, Thr, Pro and Gly;
2. Polar, negatively charged residues and their amides: Asp, Asn, Glu and Gln;
3. Polar, positively charged residues: His, Arg and Lys;
4. Large aliphatic, nonpolar residues: Met, Leu, lle, Val and Cys; and
5. Aromatic residues: Phe, Tyr and Trp.

A preferred listing of conservative substitutions, based on empirical evidence from studies on homologous protein sequences, is the following:

| Original Residue | Substitution |
|---|---|
| Ala | Gly, Ser |
| Arg | Lys |
| Asn | Gln, His |
| Asp | Glu |
| Cys | Ser |
| Gln | Asn |
| Glu | Asp |
| Gly | Ala, Pro |
| His | Asn, Gln |

-continued

| Original Residue | Substitution |
|---|---|
| Ile | Leu, Val |
| Leu | Ile, Val |
| Lys | Arg, Gln, Glu |
| Met | Leu, Tyr, Ile |
| Phe | Met, Leu, Tyr |
| Ser | Thr |
| Thr | Ser |
| Trp | Tyr |
| Tyr | Trp, Phe |
| Val | Ile, Leu |

The types of substitutions selected is preferably, but not necessarily, based on the analysis of the frequencies of amino acid substitutions between homologous proteins of different species, such as that developed by Schulz et al., *Principles of Protein Structure*, Springer-Verlag, 1978, on the analyses of structure-forming potentials developed by Chou and Fasman, *Biochemistry*, 13, 211 (1974) and *Adv. Enzymol.*, 47, 45–149 (1978), and on the analysis of hydrophobicity patterns in proteins developed by Eisenberg et al., *Proc. Natl. Acad. Sci. USA*, 81, 140–144 (1984); Kyte & Doolittle, *J. Molec. Biol.*, 157, 105–132 (1981), and Goldman et al., *Ann. Rev. Biophys. Chem.*, 15, 321–353 (1986).

GlyT DNAs that encode proteins that exhibit overall less than about 45% sequence identity with each of the proteins encoded by SEQ ID NOs:1–4 are nonetheless included as GlyT DNA to the extent that the related nucleic acid includes nucleotide and amino acid sequences specific to the genes that encode GlyT-1 or GlyT-2 or substantial portions thereof. By "substantial portions" it is intended that the included portion includes a continuous segment of at least about 50 nucleotides that encode a peptide sequence that exhibits at least about 80% amino acid sequence identity with the corresponding segment of the protein encoded by SEQ ID NOs:1, 2, 3, or 4; more preferredly, the substantial portion includes a continuous segment of at least about 500 nucleotides that encode a peptide sequence that exhibits at least about 70% amino acid sequence identity with the corresponding segment of the protein encoded by SEQ ID NOs:1, 2, 3, or 4; and yet more preferredly, the substantial portion includes a continuous segment of at least about 1000 nucleotides that encode a peptide sequence that exhibits at least about 60% amino acid sequence identity with the corresponding segment of the protein encoded by SEQ ID NOs:1, 2, 3, or 4.

As used in the context of the present invention, the specified sequence identity of a nucleic acid with respect to one of SEQ ID NOs:1–4, or substantial portions thereof, in part defines one embodiment of the GlyT DNA used to generate inventive gene constructs, vectors, and transformed hosts that can be used in the drug discovery method disclosed herein. Accordingly, the nucleic acid used in the context of the present invention is sequenced or otherwise suitably analyzed so as to compare its sequence to one of those of SEQ ID NO:1, 2, 3, or 4.

Numerous methods for determining percent sequence identity are known in the art. One preferred method is to use version 6.0 of the GAP computer program for making sequence comparisons. The program is available from the University of Wisconsin Genetics Computer Group and utilizes the alignment method of Needleman and Wunsch, *J. Mol. Biol.*, 48, 443, 1970 as revised by Smith and Waterman, *Adv. Appl. Math.*, 2, 482, 1981. Another available method uses the FASTA computer program (Pearson and Lipman, *Proc. Natl. Acad. Sci. USA*, 85, 2444–2448 (1988)).

As noted above, the present invention relates to cells transfected with GlyT DNA, which is any suitable DNA that encodes a glycine transporter such that glycine transporter properties are expressed by the transfected cells. In one embodiment, such GlyT DNA is homologous to at least one of SEQ ID NOs:1–4, or a sequence complementary thereto; a preferred GlyT DNA of this embodiment encodes a protein that has at least about 45% sequence identity with respect to at least one of SEQ ID NOs:1–4. A more preferred GlyT DNA used in the context of the present invention comprises a nucleic acid selected from the group consisting of SEQ ID NOs:1–4, a nucleic acid complementary thereto, and a substantially equivalent nucleic acid. Such related GlyT DNAs as defined hereinabove are isolated using one of the SEQ ID NOs:1–4, or substantial portions thereof, as a probe in any of a variety of conventional procedures of molecular biology, including but not limited to hybridization, PCR, or others, on genomic DNA or cDNA derived from organisms that have glycine transport activity, or on genomic or cDNA libraries derived from such organisms.

A "substantially equivalent" nucleic acid is a nucleic acid having a sequence that varies from one of SEQ ID NOs:1–4 by one or more substitutions, deletions, or additions, the effect of which does not result in an undesirable functional dissimilarity between the two nucleic acids. In other words, the polypeptide that results from the substantially equivalent sequence has the activity characteristic of the GlyT gene product. A difference in sequence at the amino acid level is understood to include amino acid differences, which range from a single amino acid substitution, deletion, or insertion to a number of amino acid substitutions, deletions, and/or insertions, wherein the resulting polypeptide is still recognizable as related to the GlyT protein in that functionality of the glycine transporter is preserved.

A method for the analysis or screening of an agent for treatment of a disease or condition associated with a nervous system disorder or condition comprises culturing separately first and second non-mammalian cells, wherein the first and second non-mammalian cells are preferably of the same species, more preferably of the same strain thereof, and comprise an exogenous nucleic acid encoding a glycine transporter as described herein, preferably either GlyT-1 or GlyT-2, wherein GlyT-1 is GlyT-1a, GlyT-1b, or GlyT-1c. The nervous system disorders or conditions for which the agent can be used for treatment include, but are not limited to, spasticity, myoclonus, muscle spasm, pain, muscle hyperactivity, epilepsy, stroke, head trauma, neuronal cell death, cognitive or memory disorders, multiple sclerosis, spinal cord injury, dystonia, Alzheimer's disease, Huntington's disease, amyotrophic lateral sclerosis, attention deficit disorders, organic brain syndromes, and schizophrenia. In this method, the first non-mammalian cell is contacted with the agent, which is preferably a compound, such as a peptide or an organic compound, or a composition or mixture comprising same, as further discussed below, in the presence of a suitably-labeled glycine. Such a labeled glycine has incorporated into it, for example, a radioisotope, such as $^3$H or $^{14}$C. The contacted first non-mammalian cell is then tested for enhancement or inhibition of glycine transport into the first non-mammalian cell as compared to glycine transport into the second non-mammalian cell that was not contacted with the compound (i.e., the control cell). Such analysis or screening preferably includes activities of finding, learning, discovering, determining, identifying, or ascertaining.

An agent is an enhancer of glycine transport uptake if at the end of the aforestated test the amount of intracellular labeled glycine is greater in the agent-contacted non-mammalian cell than in the non-agent-contacted non-mammalian cell; conversely, an agent is an inhibitor of glycine transport if the amount of intracellular labeled glycine is greater in the non-agent-contacted non-mammalian cell as compared to the other. Preferably, the difference in glycine uptake between the tested first cell and the control second cell is at least about a factor of two; more preferably, the difference is at least about a factor of five; most preferably, the difference is at least about an order of magnitude or greater.

Agents identified using the inventive method are specific for GlyT-1a, GlyT-1b, GlyT-1c, GlyT-2, or any combination thereof. The same compound preferably is an inhibitor or an enhancer with respect to any one glycine transporter, but may have a neutral or opposite effect with another glycine transporter. Preferred agents have specificity to enhance or inhibit one glycine transporter and have neutral or negligible effect on other glycine transporters as compared to the effect on the indicated glycine transporter. Preferably, an agent having specificity for one glycine transporter with respect to a second glycine transporter has at least an order of magnitude greater potency for inhibiting or activating glycine uptake mediated by the first glycine transporter as compared to its effect on the second glycine transporter, as tested in transfected cells of the present invention. More preferred agents have differences in potency of at least two orders of magnitude for one glycine transporter as compared to the other.

An agent can be any suitable compound, material, composition, mixture, or chemical, including but not limited to polypeptides of two up to about 25 amino acids in length, preferably from two to about ten, more preferably from two to about five amino acids in length. Other suitable agents in the context of the present invention include small organic compounds, of molecular weight between about 100 daltons and about 5,000 daltons, and are composed of alkyls, aryls, alkenes, alkynes, and other suitable groups, including heteroatoms or not. Such organic compounds can be carbohydrates, including simple sugars, amino or imino acids, nucleic acids, steroids, and others. The chemicals tested as agents hereby may be prepared using combinatorial chemical processes known in the art or conventional means for chemical synthesis. Preferably, suitable agents are useful as drugs for treatment of the aforementioned or other nervous system disorders or conditions.

Agents identified that enhance or inhibit the glycine transporter, or inhibit or activate the glycine receptor portion of the NMDA receptor, using the methods described herein, include those wherein the agent is of the formula:

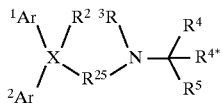

or a pharmaceutically acceptable salt thereof, wherein:
(1) X is nitrogen or carbon;
(2) $Ar^1$ is aryl, heteroaryl, arylalkyl wherein the alkyl is C1 to C2,
or heteroarylalkyl wherein the alkyl is C1 to C2, and $Ar^2$ is aryl, heteroaryl, aryloxy, heteroaryloxy, arylalkyl wherein the alkyl is C1 to C2, heteroarylalkyl wherein the alkyl is C1 to C2, arylmethoxy, heteroarylmethoxy, arylthio, heteroarylthio, arylmethylthio, heteroarylmethylthio, or either Ar—N($R^6$)— or Ar—$CH_2$—N($R^{6*}$)—, wherein $R^6$ and $R^{6*}$ are hydrogen or (C1–C6) alkyl and Ar is aryl or heteroaryl,
(a) wherein when X is nitrogen $Ar^2$ is not aryloxy, heteroaryloxy, arylmethoxy, heteroarylmethoxy, arylthio, heteroarylthio, arylmethylthio, heteroarylmethylthio, Ar—N($R^6$)— or Ar—$CH_2$—N($R^{6*}$)—,
(b) wherein the aryl of $Ar^1$ or $Ar^2$ is phenyl or naphthyl,
(c) wherein the heteroaryl of $Ar^1$ or $Ar^2$ comprises a five-membered ring, a six-membered ring, a six-membered ring fused to a five-membered ring, or a six-membered ring fused to a six-membered ring, wherein the heteroaryl is aromatic and contains heteroatoms selected from the group consisting of oxygen, sulfur and nitrogen, with the remaining ring atoms being carbon,
(d) wherein the aryl or heteroaryl of $Ar^1$ and $Ar^2$ together can be substituted with up to six substituents selected from the group consisting of fluoro, chloro, bromo, nitro, cyano, trifluoromethyl, amidosulfonyl which can have up to two (C1–C6) N-alkyl substitutions, (C1–C6) alkyl, (C2–C6) alkenyl, amino, (C1–C6) alkylamino, dialkylamino wherein each alkyl is independently C1 to C6, (C1–C6) alkoxy, (C2–C7) alkanoyl, (C2–C7) alkanoyloxy, trifluoromethoxy, hydroxycarbonyl, (C2–C7) alkyloxycarbonyl, aminocarbonyl that can be substituted for hydrogen with up to two (C1–C6) alkyl, (C1–C6) alkylsulfonyl, amidino that can independently substituted with up to three (C1–C6) alkyl, or methylenedioxy or ethylenedioxy with the two oxygens bonded to adjacent positions on the aryl or heteroaryl ring structure, which methylenedioxy or ethylenedioxy can be substituted with up to two (C1–C6) alkyl,
(i.) wherein such substitutions to the aryl or heteroaryl of $Ar^1$ and $Ar^2$ can be combined to form a second bridge between $Ar^1$ and $Ar^2$ comprising (1) (C1–C2) alkyl or alkenyl, which can be independently substituted with one or more (C1–C6) alkyl, (2) sulfur, (3) oxygen, (4) amino, which can be substituted for hydrogen with one (C1–C6) alkyl, (5) carbonyl, (6) —$CH_2$C(=O)—, which can be substituted for hydrogen with up to two (C1–C6) alky), (7) —C(=O)—O—, (8) —$CH_2$—O—, which can be substituted for hydrogen with up to two (C1–C6) alkyl, (9) — C(=O)—N($R^{24}$)—, wherein $R^{24}$ is hydrogen or (C1–C6) alkyl, (10) —$CH_2$—NH—, which can be substituted for hydrogen with up to three (C1–C6) alkyl, (11) —CH=N—, which can be substituted for hydrogen with (C1–C6) alkyl, or wherein the aryls or heteroaryls of $Ar^1$ and $Ar^2$ can be directly linked by a single bond;
(3) $R^{25}$ comprises (a) a straight-chained (C1–C4) aliphatic group,
(b) =N—O—($R^{26}$) when X is carbon, wherein $R^{26}$ is ethylene or propylene and the unmatched double bond is linked to X, or (c) —O—$R^8$ or —S—$R^{8*}$ when X is carbon and $Ar^2$ is neither Ar—N($R^6$)— nor Ar—$CH_2$—N($R^{6*}$)—, wherein $R^8$ or $R^{8*}$ is a (C2–C3) alkylene or (C2–C3) alkenylene and O or S is bonded to X,
(i.) wherein $R^{25}$ can be substituted with up to one hydroxy, up to one (C1–C6) alkoxy or up to one (C2–C7) alkanoyloxy, with up to two (C1–C6) alkyl, with up to one oxo, up to one (C1–C6) alkylidene, with the proviso that the hydroxy, alkoxy, alkanoyloxy or oxo substituents are not bonded to a carbon that is bonded to a nitrogen or oxygen,
(ii.) wherein the alkyl or alkylidene substituents of $R^{25}$ can be linked to form a 3 to 7-membered ring,
(iii.) wherein if X is nitrogen, X is linked to $R^{25}$ by a single bond and the terminal carbon of $R^{25}$ that links $R^{25}$ to N is saturated;

(4) R² (a) is not present when X is nitrogen, (b) is hydrogen, (C1–C6) alkyl, (C1–C6) alkoxy, cyano, (C2–C7) alkanoyl, aminocarbonyl, (C1–C6) alkylaminocarbonyl, dialkylaminocarbonyl wherein each alkyl is independently C1–C6, or Ar⁹ where Ar⁹ is independently as defined for Ar¹, (c) comprises, where R²⁵ is not —O—R⁸, hydroxy, fluoro, chloro, bromo or (C2–C7) alkanoyloxy, (d) forms a double bond with an adjacent carbon or nitrogen from R²⁵;

(5) R³ (a) is hydrogen, (C1–C6) alkyl, or phenyl or phenylalkyl wherein the alkyl is C1–C6 and either such phenyl can be substituted with up to 3 of the same substituents defined above for the aryl or heteroaryl of Ar¹ or Ar², (b) is —CH(R⁹)—R¹⁰, wherein R⁹ is the same as R⁴ and R¹⁰ is the same as R⁵, or (c)Z(Ar³)(Ar⁴)(R¹¹)—R¹², wherein R¹² is bonded to N, Z is independently the same as X, Ar³ is independently the same as Ar¹, Ar⁴ is independently the same as Ar², R¹¹ is independently the same as R² and R¹² is independently the same as R²⁵;

(6) R⁴ and R⁴* are independently hydrogen or (C1–C6) alkyl that can be bonded to complete a 3 to 7-membered ring, or one of R⁴ and R⁴* can be (C1–C6) hydroxyalkyl; and (7) R⁵ is (CO)NR¹³R¹⁴, (CO)OR¹⁵, (CO)SR¹⁶, (SO₂)NR¹⁷R¹⁸, (PO)(OR¹⁹)(OR²⁰) or CN, wherein R¹³, R¹⁴, R¹⁵, R¹⁶ R¹⁷, R¹⁸ R¹⁹ and R²⁰ are independently hydrogen, (C1–C8) alkyl which can incorporate a (C3–C8) cycloalkyl, wherein the carbon linked to the oxygen of R¹⁵ or the sulfur of R¹⁶ has no more than secondary branching and, (C2–C6) hydroxyalkyl, aminoalkyl where the alkyl is C2–C6 and the amino can be substituted with up to two (C1–C6) alkyls, arylalkyl wherein the alkyl is C1 to C6, heteroarylalkyl wherein the alkyl is C1 to C6, aryl or heteroaryl, (a) wherein the aryl is phenyl or napthyl and the heteroaryl is a five-membered ring, a six-membered ring, a six-membered ring fused to a five-membered ring, or a six-membered ring fused to a six-membered ring, wherein the heteroaryl is aromatic and contains heteroatoms selected from the group consisting of oxygen, sulfur and nitrogen, with the remaining ring atoms being carbon, (b) wherein the aryl, heteroaryl, aryl or arylalkyl or the heteroaryl of heteroarylalkyl can be substituted with up to three substituents selected from the group consisting of fluoro, chloro, bromo, nitro, cyano, trifluoromethyl, amidosulfonyl which can have up to two (C1–C6) N-alkyl substitutions, (C1–C6) alkyl, (C2–C6) alkenyl, (C1–C6) alkylamine, dialkylamine wherein each alkyl is independently C1 to C6, amino, (C1–C6) alkoxy, (C2–C7) alkanoyl, (C2–C7) alkanoyloxy, trifluoromethoxy, hydroxycarbonyl, (C2–C7) alkyloxycarbonyl, aminocarbonyl that can be N-substituted with up to two (C1–C6) alkyl, (C1–C6) alkylsulfonyl, amidino that can substituted with up to 3 (C1–C6) alkyl, or methylenedioxy or ethylenedioxy with the two oxygens bonded to adjacent positions on the aryl or heteroaryl ring structure, which methylenedioxy or ethylenedioxy can be substituted with up to two (C1–C6) alkyl, and (c) wherein R¹³ and R¹⁴ together with the nitrogen can form a 5 to 7-membered ring that can contain one additional heteroatom selected from oxygen and sulfur. Other suitable agents identified as above include those wherein the agent is of the formula:

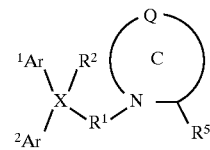

or a pharmaceutically acceptable salt thereof, wherein:

(1) X is nitrogen or carbon;

(2) Ar¹ is aryl, heteroaryl, arylalkyl wherein the alkyl is C1 to C2, or heteroarylalkyl wherein the alkyl is C1 to C2, and Ar² is aryl, heteroaryl, aryloxy, heteroaryloxy, arylalkyl wherein the alkyl is C1 to C2, heteroarylalkyl wherein the alkyl is C1 to C2, arylmethoxy, heteroarylmethoxy, arylthio, heteroarylthio, arylmethylthio, heteroarylmethylthio, or either Ar—N(R⁶)— or Ar—CH₂—N(R⁶*)—, wherein R⁶ and R⁶* are hydrogen or (C1–C6) alkyl and Ar can be aryl or heteroaryl, (a) wherein when X is nitrogen Ar² is not aryloxy, heteroaryloxy, arylmethoxy, heteroarylmethoxy, arylthio, heteroarylthio, arylmethylthio, heteroarylmethylthio, Ar—N(R⁶)— or Ar—CH₂—N(R⁶*)—, (b) wherein the aryl of Ar¹ or Ar² is phenyl or naphthyl, (c) wherein the heteroaryl of Ar¹ or Ar² comprises a five membered ring, a six-membered ring, a six-membered ring fused to a five-membered ring, or a six-membered ring fused to a six-membered ring, wherein the heteroaryl is aromatic and contains heteroatoms selected from the group consisting of oxygen, sulfur and nitrogen, with the remaining ring atoms being carbon, (d) wherein the aryl or heteroaryl of Ar¹ and Ar² together can be substituted with up to six substituents selected from the group consisting of fluoro, chloro, bromo, nitro, cyano, trifluoromethyl, amidosulfonyl which can have up to two (C1–C6) N-alkyl substitutions, (C1–C6) alkyl, (C2–C6) alkenyl, amino, (C1–C6) alkylamino, dialkylamino wherein each alkyl is independently C1 to C6, (C1–C6) alkoxy, (C2–C7) alkanoyl, (C2–C7) alkanoyloxy, trifluoromethoxy, hydroxycarbonyl, (C2–C7) alkyloxycarbonyl, aminocarbonyl that can be substituted for hydrogen with up to two (C1–C6) alkyl, (C1–C6) alkylsulfonyl, amidino that can independently substituted for hydrogen with up to three (C1 –C6) alkyl, or methylenedioxy or ethylenedioxy with the two oxygens bonded to adjacent positions on the aryl or heteroaryl ring structure, which methylenedioxy or ethylenedioxy can be substituted with up to two (C1–C6) alkyl, (i.) wherein such substitutions to the aryl or heteroaryl of Ar¹ and Ar² can be combined to form a second bridge between Ar¹ and Ar² comprising (1) (C1–C2) alkyl or alkenyl, which can be independently substituted with one or more (C1–C6) alkyl, (2) sulfur, (3) oxygen, (4) amino, which can be substituted for hydrogen with one (C1–C6) alkyl, (5) carbonyl, (6) —CH₂C(=O)—, which can be substituted for hydrogen with up to two (C1–C6) alkyl, (7) —C(=O)—O—, (8) —CH₂—O—, which can be substituted for hydrogen with up to two (C1–C6) alkyl, (9) —C(=O)—N(R²⁴)—, wherein R²⁴ is hydrogen or (C1–C6) alkyl, (10) —CH₂—NH—, which can be substituted for hydrogen with up to three (C1–C6) alkyl, or (11) —CH=N—, which can be substituted for hydrogen with (C1–C6) alkyl, or wherein the aryls or heteroaryls of $Ar^1$ and $Ar^2$ can be directly linked by a single bond;

(3) $R^1$ comprises (a) a straight-chained (C2–C4) aliphatic group, (b) =N—O—(CH$_2$CH$_2$)—when X is carbon, wherein the unmatched double bond is linked to X, or (c) —O—$R^8$ or —S—$R^{8*}$ — when X is carbon and $Ar^2$ is neither Ar—N($R^6$)— nor Ar—CH$_2$—N($R^{6*}$)—, wherein $R^8$ or $R^{8*}$ is a (C2–C3) alkylene or (C2–C3) alkenylene and O or S is bonded to X, (i.) wherein $R^1$ can be substituted with up to one hydroxy, up to one (C1–C6) alkoxy or up to one (C2–C7) alkanoyloxy, with up to two (C1–C6) alkyl, with up to one oxo, up to one (C1–C6) alkylidene, with the proviso that the hydroxy, alkoxy, alkanoyloxy or oxo substituents are not bonded to a carbon that is bonded to a nitrogen or oxygen, (ii.) wherein the alkyl or alkylidene substituents of $R^1$ can be linked to form a 3 to 7-membered ring, (iii.) wherein if X is nitrogen, X is linked to $R^1$ by a single bond and wherein the terminal carbon of $R^1$ that links $R^1$ to N is saturated;

(4) $R^2$ (a) is not present when X is nitrogen, (b) is hydrogen, (C1–C6) alkyl, (C1–C6) alkoxy, cyano, (C2–C7) alkanoyl, aminocarbonyl, (C1–C6) alkylaminocarbonyl or dialkylaminocarbonyl wherein each alkyl is independently C1 to C6, (c) comprises, where $R^1$ is not —O—$R^8$ or —S—$R^{8*}$—, hydroxy, fluoro, chloro, bromo or (C2–C7) alkanoyloxy, (d) forms a double bond with an adjacent carbon or nitrogen from R1;

(5) wherein Q together with the illustrated tertiary nitrogen and tertiary carbon bearing $R^5$ form ring C, wherein ring C is a 3 to 8-membered ring, a 3 to 8-membered ring substituted with a 3 to 6-membered spiro ring, or a 3 to 8-membered ring fused with a 5 to 6-membered ring, wherein the fused ring lacking the illustrated tertiary nitrogen can be aromatic or heteroaromatic, wherein for each component ring of ring C there are up to two heteroatoms selected from oxygen, sulfur or nitrogen, including the illustrated nitrogen, and the rest carbon, with the proviso that the ring atoms include no quaternary nitrogens, with the proviso that, in saturated rings, ring nitrogen atoms are separated from other ring heteroatoms by at least two intervening carbon atoms, (a) wherein the carbon and nitrogen ring atoms of ring C can be substituted with up to three substituents selected from (C1–C6) alkyl, (C2–C6) alkenylene, cyano, nitro, trifluoromethyl, (C2–C7) alkyloxycarbonyl, (C1–C6) alkylidene, hydroxyl, (C1–C6) alkoxy, oxo, hydroxycarbonyl, aryl wherein the aryl is as defined for $Ar^1$ or heteroaryl wherein the heteroaryl is as defined for $Ar^1$, with the proviso that ring atoms substituted with alkylidene, hydroxycarbonyl or oxo are carbon, with the further proviso that ring atoms substituted with hydroxyl or alkoxy are separated from other ring heteroatoms by at least two intervening carbon atoms, (b) and wherein Q is as appropriate to satisfy the definition of ring C; and (6) $R^5$ is (CO)$NR^{13}R^{14}$, (CO)$OR^{15}$, (CO)$SR^{16}$, (SO$_2$)$NR^{17}R^{18}$, (PO)($OR^{19}$)($OR^{20}$) or CN, wherein $R^{13}$, $R^{14}$, $R^{15}$, $R^{16}$ $R^{17}$, $R^{18}$ $R^{19}$ and R20 are independently hydrogen, (C1–C8) alkyl which can incorporate a (C3–C8) cycloalkyl, wherein the carbon linked to the oxygen of $R^{15}$ or the sulfur of $R^{16}$ has no more than secondary branching and, (C2–C6) hydroxyalkyl, aminoalkyl where the alkyl is C2 to C6 and the amino can be substituted with up to two (C1–C6) alkyls, arylalkyl wherein the alkyl is C1 to C6, heteroarylalkyl wherein the alkyl is C1 to C6, aryl or heteroaryl, (a) wherein the aryl is phenyl or napthyl and the heteroaryl is a five-membered ring, a six-membered ring, a six-membered ring fused to a five-membered ring, or a six-membered ring fused to a six-membered ring, wherein the heteroaryl is aromatic and contains heteroatoms selected from the group consisting of oxygen, sulfur and nitrogen, with the remaining ring atoms being carbon, (b) wherein the aryl, heteroaryl, aryl or arylalkyl or the heteroaryl of heteroarylalkyl can be substituted with up to three substituents selected from the group consisting of fluoro, chloro, bromo, nitro, cyano, trifluoromethyl, amidosulfonyl which can have up to two (C1–C6) N-alkyl substitutions, (C1–C6) alkyl, (C2–C6) alkenyl, (C1–C6) alkylamine, dialkylamine wherein each alkyl is independently C1 to C6, amino, (C1–C6) alkoxy, (C2–C7) alkanoyl, (C2–C7) alkanoyloxy, trifluoromethoxy, hydroxycarbonyl, (C2–C7) alkyloxycarbonyl, aminocarbonyl that can be N-substituted with up to two (C1–C6) alkyl, (C1–C6) alkylsulfonyl, amidino that can substituted for hydrogen with up to three (C1–C6) alkyl, or methylenedioxy or ethylenedioxy with the two oxygens bonded to adjacent positions on the aryl or heteroaryl ring structure, which methylenedioxy or ethylenedioxy can be substituted with up to two (C1–C6) alkyl, (c) wherein $R^{13}$ and $R^{14}$ together with the nitrogen to which they are bonded can form a 5 to 7-membered ring that can contain one additional heteroatom selected from oxygen and sulfur.

Yet other suitable agents identified as above include those wherein the agent is of the following formula 1 or 1l:

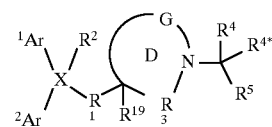

I

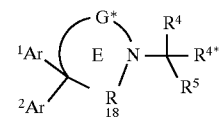

II or a pharmaceutically acceptable salt thereof, wherein:

(1) X is nitrogen or carbon;

(2) $Ar^1$ is aryl, heteroaryl, arylalkyl wherein the alkyl is C1 to C2, or heteroarylalkyl wherein the alkyl is C1 to C2, and $Ar^2$ is aryl, heteroaryl, aryloxy, heteroaryloxy, arylalkyl wherein the alkyl is C1 to C2, heteroarylalkyl wherein the alkyl is C1 to C2, arylmethoxy, heteroarylmethoxy, arylthio, heteroarylthio, arylmethylthio, heteroarylmethylthio, or either Ar—N($R^6$)— or Ar—CH$_2$—N($R^{6*}$)—, wherein $R^6$ and $R^{6*}$ are hydrogen or (C1–C6) alkyl and Ar can be aryl or heteroaryl, (a) wherein when X is nitrogen $Ar^2$ is not aryloxy, heteroaryloxy, arylmethoxy, heteroarylmethoxy, arylthio, heteroarylthio, arylmethylthio, heteroarylmethylthio, Ar—N($R^6$)—or Ar—CH$_2$—N($R^{6*}$)—, (b) wherein the aryl of $Ar^1$ or $Ar^2$ is phenyl or naphthyl, (c) wherein the heteroaryl of $Ar^1$ or $Ar^2$ comprises a five-membered ring, a six-membered ring, a six-membered ring fused to a five-membered ring, or a six-membered ring fused to a six-membered ring, wherein the heteroaryl is aromatic and contains heteroatoms selected from the group consisting of oxygen, sulfur and nitrogen, with the remaining ring atoms being carbon, (d) wherein the aryl or heteroaryl of $Ar^1$ and $Ar^2$ together can be substituted with up to six substituents selected from the group consisting of fluoro, chloro, bromo, nitro, cyano, trifluoromethyl, amidosulfonyl which can have up to two (C1–C6) N-alkyl substitutions, (C1–C6) alkyl, (C2–C6) alkenyl, amino, (C1–C6) alkylamino, dialkylamino wherein each alkyl is independently C1 to C6, (C1–C6) alkoxy, (C2–C7) alkanoyl, (C2–C7) alkanoyloxy, trifluoromethoxy, hydroxycarbonyl, (C2–C7) alkyloxycarbonyl, aminocarbonyl that can be substituted for hydrogen with up to two (C1–C6) alkyl, (C1–C6) alkylsulfonyl, amidino that can independently substituted for hydrogen with up to three (C1–C6) alkyl, or methylenedioxy or ethylenedioxy with the two oxygens bonded to adjacent positions on the aryl or heteroaryl ring structure, which methylenedioxy or ethylenedioxy can be substituted with up to 2 (C1–C6) alkyl, (i.) wherein such substitutions to the aryl or heteroaryl of $Ar^1$ and $Ar^2$ can be combined to form a second bridge between $Ar^1$ and $Ar^2$ comprising (1) (C1–C2) alkyl or alkenyl, which can be substituted with one or more (C1–C6) alkyl, (2) sulfur, (3) oxygen, (4) amino, which can be substituted for hydrogen with one (C1–C6) alkyl, (5) carbonyl, (6) —$CH_2C(=O)$—, which can be substituted for hydrogen with up to two (C1–C6) alkyl, (7) —C(=O)—O—, (8) —$CH_2$—O—, which can be substituted for hydrogen with up to two (C1–C6) alkyl, (9) —C(=O)—N($R^{24}$)—, wherein $R^{24}$ is hydrogen or (C1–C6) alkyl, (10) —$CH_2$—NH—, which can be substituted for hydrogen with up to three (C1–C6) alkyl, or (11) —CH=N—, which can be substituted for hydrogen with (C1–C6) alkyl, or wherein the aryls or heteroaryls of $Ar^1$ and $Ar^2$ can be directly linked by a single bond;

(3) $R^1$ comprises (a) a single bond or double bond, (b) a straight-chained (C1–C3) aliphatic group, (c) =N—O—($CH_2CH_2$)— when X is carbon, wherein the unmatched double bond is linked to X, or (d) —O—$R^8$ or —S—$R^{8*}$ when X is carbon and $Ar^2$ is neither Ar—N($R^6$)— nor Ar—$CH_2$—N($R^{6*}$)—, wherein either $R^8$ or $R^{8*}$ is a single bond, (C1–C3) alkylene or (C2–C3) alkenylene and O or S is bonded to X, (i.) wherein $R^1$ can be substituted with up to one hydroxy, up to one (C1–C6) alkoxy or up to one (C2–C7) alkanoyloxy, with up to two (C1–C6) alkyl, with up to one oxo, up to one (C1–C6) alkylidene, with the proviso that the hydroxy, alkoxy, alkanoyloxy or oxo substituents are not bonded to a carbon that is bonded to a nitrogen or oxygen, (ii.) wherein the alkyl or alkylidene substituents of $R^1$ can be linked to form a 3 to 7-membered ring, (iii.) wherein if X is nitrogen, X is linked to $R^1$ by a single bond and the terminal carbon of $R^1$ that links $R^1$ to N is saturated;

(4) $R^2$ (a) is not present when X is nitrogen, (b) is hydrogen, (C1–C6) alkyl, (C1–C6) alkoxy, cyano, (C2–C7) alkanoyl, aminocarbonyl, (C1–C6) alkylaminocarbonyl or dialkylaminocarbonyl wherein each alkyl is independently C1–C6, (c) comprises, where $R^1$ is not —O—$R^8$, hydroxy, fluoro, chloro, bromo or(C2–C7) alkanoyloxy, (d) forms a double bond with an adjacent carbon or nitrogen from R1;

(5) $R^3$ is a single bond or (C1–C2) alkyl or alkenyl;

(6) $R^{18}$ is a single bond or (C1–C3) alkyl or alkenyl;

(7) wherein ring D is a 3 to 8-membered ring, a 3 to 8-membered ring substituted with a 3 to 6-membered spiro ring, or a 3 to 8-membered ring fused with a 5 to 6-membered ring, wherein the fused ring lacking the illustrated tertiary nitrogen can be aromatic or heteroaromatic, wherein for each component ring of ring D there are up to two heteroatoms selected from oxygen, sulfur or nitrogen, including the illustrated nitrogen, and the rest carbon, with the proviso that the ring atoms include no quaternary nitrogens, with the proviso that, in saturated rings, ring nitrogen atoms are separated from other ring heteroatoms by at least two intervening carbon atoms, (a) wherein the carbon and nitrogen ring atoms of ring D can be substituted with up to three substituents selected from (C1–C6) alkyl, (C2–C6) alkenylene, cyano, nitro, trifluoromethyl, (C2–C7) alkyloxycarbonyl, (C1–C6) alkylidene, hydroxyl, (C1–C6) alkoxy, oxo, hydroxycarbonyl, aryl wherein the aryl is as defined for $Ar^1$ or heteroaryl wherein the heteroaryl is as defined for $Ar^1$, with the proviso that ring atoms substituted with alkylidene, hydroxycarbonyl or oxo are carbon, with the further proviso that ring atoms substituted with hydroxyl or alkoxy are separated from other ring heteroatoms by at least two intervening carbon atoms, (b) and wherein G is a required to satisfy the definition of ring D;

(8) wherein ring E is a 3 to 8-membered ring, a 3 to 8-membered ring substituted with a 3 to 6-membered spiro ring, or a 3 to 8-membered ring fused with a 5 to 6-membered ring, wherein the fused ring lacking the illustrated tertiary nitrogen can be aromatic or heteroaromatic, wherein for each component ring of ring E there are up to two heteroatoms selected from oxygen, sulfur or nitrogen, including the illustrated nitrogen, and the rest carbon, with the proviso that the ring atoms include no quaternary nitrogens, with the proviso that, in saturated rings, ring nitrogen atoms are separated from other ring heteroatoms by at least two intervening carbon atoms, (a) wherein the carbon and nitrogen ring atoms of ring E can be substituted with up to three substituents selected from (C1–C6) alkyl, (C2–C6) alkenylene, cyano, nitro, trifluoromethyl, (C2–C7) alkyloxycarbonyl, (C1–C6) alkylidene, hydroxyl, (C1–C6) alkoxy, oxo, hydroxycarbonyl, (C1–C6) alkoxycarbonyl, aryl wherein the aryl is as defined for $Ar^1$ or heteroaryl wherein the heteroaryl is as defined for $Ar^1$, with the proviso that ring atoms substituted with alkylidene, hydroxycarbonyl or oxo are carbon, with the further proviso that ring atoms substituted with hydroxyl or alkoxy are separated from other ring heteroatoms by at least two intervening carbon atoms;

(b) and wherein $G^*$ is a required to satisfy the definition of ring E;

(9) $R^{19}$ (a) forms a double bond with $R^1$, $R^3$ or G, (b) is hydrogen (c) is (C1–C3) alkyl or alkylene, or (d) is incorporated into a fused ring;

(10) $R^4$ and $R^{4*}$ are independently hydrogen or (C1–C6) alkyl that can be bonded to complete a 3 to 7-membered ring, or one of $R^4$ and $R^{4*}$ can be (C1–C6) hydroxyalkyl; and

(11) $R^5$ is $(CO)NR^{13}R^{14}$, $(CO)OR^{15}$, $(CO)SR^{16}$, $(SO_2)NR^{17}R^{18}$, $(PO)(OR^{21})(OR^{20})$ or CN, wherein $R^{13}$, $R^{14}$, $R^{15}$, $R^{16}$, $R^{17}$, $R^{18}$, $R^{2}$ $R^{20}$ are independently hydrogen, (C1–C8) alkyl which can incorporate a (C3–C8) cycloalkyl, wherein the carbon linked to the oxygen of $R^{15}$ or the sulfur of $R^{16}$ has no more than secondary branching and, (C2–C6) hydroxyalkyl, aminoalkyl where the alkyl is C2 to C6 and the amino can be substituted with up to two (C1–C6) alkyls, arylalkyl wherein the alkyl is C1 to C6, heteroarylalkyl wherein the alkyl is C1 to C6, aryl or heteroaryl, (a) wherein the aryl is phenyl or napthyl and the heteroaryl is a five-membered ring, a six-membered ring, a six-membered ring fused to a five-membered ring, or a six-membered ring fused to a six-membered ring, wherein the heteroaryl is aromatic and contains heteroatoms selected from the group consisting of oxygen, sulfur and nitrogen, with the remaining ring atoms being carbon, (b) wherein the aryl, heteroaryl, aryl or arylalkyl or the heteroaryl of heteroarylalkyl can be substituted with up to three substituents selected from the group consisting of fluoro, chloro, bromo, nitro, cyano, trifluoromethyl, amidosulfonyl which can have up to two (C1–C6) N-alkyl substitutions, (C1–C6) alkyl, (C2–C6) alkenyl, (C1–C6) alkylamine, dialkylamine wherein each alkyl is independently C1 to C6, amino, (C1–C6) alkoxy, (C2–C7) alkanoyl, (C2–C7) alkanoyloxy, trifluoromethoxy, hydroxycarbonyl, (C2–C7) alkyloxycarbonyl, aminocarbonyl that can be N-substituted with up to two (C1–C6) alkyl, (C1–C6) alkylsulfonyl, amidino that can substituted with up to three (C1–C6) alkyl, or methylenedioxy or ethylenedioxy with the two oxygens bonded to adjacent positions on the aryl or heteroaryl ring structure, which methylenedioxy or ethylenedioxy can be substituted with up to two (C1–C6) alkyl, and (c) wherein $R^{13}$ and $R^{14}$ together with the nitrogen can form a 5 to 7-membered ring that can contain one additional heteroatom selected from oxygen and sulfur.

Some compounds that inhibit GlyT-1 or GlyT-2 mediated transport also bind to the glycine binding site on the NMDA receptor. Such binding can be identified by a binding assay whereby, for example, radiolabelled glycine is placed in contact with a preparation of NMDA receptors, such as can be prepared from neuronal cells or brain tissue. See, for example, Grimwood et al., *Molec. Pharmacol.*, 41, 923–930 (1992). In particular, one can prepare such NMDA receptors by isolating a membrane fraction from selected brain tissue of a suitable animal. Suitable brain tissue includes, but is not limited to, cortices and hippocampi, as isolated from any mammal. A membrane fraction can be prepared therefrom using conventional means, and includes, for example, methods of homogenization and centrifugation. The NMDA receptor located in such membranes is treated using mild detergent, such as about 0.1% to about 0.5% saponin, to remove any endogenous glycine or glutamate. The glycine used in such an assay is radiolabelled with any suitable isotope, such as $^{14}C$ or $^{3}H$.

Specific binding of the radiolabelled glycine is then determined by subtracting the quantified radioactivity due to non-specific binding from that which is due to total (i.e., specific and non-specific) binding of the radiolabelled glycine. The radioactivity due to non-specific binding is determined by quantifying the amount of radiolabel associated with an NMDA receptor-containing membrane fraction that has been contacted with radiolabelled glycine and with at least a 100-fold excess of non-radiolabelled or "cold" glycine. The radioactivity due to total binding of the radiolabelled glycine is determined by quantifying the amount of radiolabel bound to the NMDA receptor preparation in the absence of non-radiolabeled glycine. One can also measure binding to the glycine site on the NMDA receptor using labeled analogs of amino acids, such as, for example, dichlorokynurenic acid or L-689,560. See Grimwood et al., *Molecular Pharmacol.*, 49, 923–930 (1992).

Another way to measure binding of a compound to the glycine site on the NMDA receptor is by measuring the compound's ability to modulate the binding of $[^{3}H]MK-801$ to the NMDA receptor. MK-801 binds to the NMDA receptor at a different site than does glycine, but binding of glycine or other ligands to the glycine site can allosterically modulate the binding of MK-801. An advantage of this technique is that it allows one to distinguish compounds having agonist activity from those having antagonist activity at the NMDA-receptor-glycine binding site. In particular, compounds having agonist activity in this assay enhance MK-801 binding; conversely, compounds having antagonist activity inhibit MK-801 binding. Sterner and Calligaro, *Soc. Neurosci. Abstr.*, 21, 351 (1995); Calligaro et al., *J. Neurochem.*, 60, 2297–2303 (1993).

A functional ion-flux assay used to measure the effect of compounds identified by the present invention relates to the ability to enhance or inhibit calcium flux through the NMDA receptor. This test is performed on suitable cell cultures that have membrane-bound NMDA receptors and glycine transporters. Such cells include neuronal cells generally, including those of the central nervous system, including brain, and cell lines derived therefrom, and any other cell that has been induced or transfected to express NMDA receptors. Calcium used in such a test is commonly the $^{45}Ca$ isotope, although other calcium measuring techniques can be used as well, such as calcium-associated fluorescence and the like. However the calcium is monitored, calcium flux is enhanced or inhibited as a result of the discrete addition of a compound of the present invention. An advantage of this system is that it allows one to monitor the net effect on NMDA receptor function of a compound that interacts with the glycine site on the NMDA receptor and the glycine transporter.

GlyT-1 inhibitors that are also NMDA receptor agonists act to alleviate schizophrenia and enhance cognition both by increasing glycine concentrations at the NMDA receptor-expressing synapses via inhibition of the glycine transporter, and via directly enhancing NMDA receptor activity. Glycine transporter inhibitors that are also NMDA receptor antagonists can nonetheless retain activity in schizophrenia and enhancing cognition, if the increase in glycine due to glycine transport inhibition prevails over the NMDA antagonism. Where the NMDA receptor antagonist activity prevails over the effect of increased extracellular glycine resulting from inhibition of the glycine transporter, these compounds are useful in limiting the cell damage and cell death arising after stroke or as a consequence of neurodegenerative diseases such as Alzheimer's, Parkinson's, AIDS dementia, Huntington's, and the like. See, for example, Choi, supra; Coyle and Puttfarcken, supra; Lipton and Rosenberg, supra; Brennan, *Chem. Eng. News* (May 13, 1996), pp. 41–47; Leeson, in *Drug Design For Neuroscience* (Alan P. Kozikowski, ed., 1993), pp. 339–383.

As discussed above, the compounds of the invention have a number of pharmacological actions. The relative effectiveness of the compounds can be assessed in a number of ways, including the following:

1. Comparing the activity mediated through GlyT-1 and GlyT-2 transporters. This testing identifies compounds (a) that are more active against GlyT-1 transporters and thus more useful in treating or preventing schizophrenia, increasing cognition and enhancing memory or (b) that are more active against GlyT-2 transporters and thus more useful in treating or preventing epilepsy, pain or spasticity.
2. Testing for NMDA receptor binding. This test establishes whether there is sufficient binding at this site, whether antagonist or agonist activity, to warrant further examination of the pharmacological effect of such binding.
3. Testing the activity of the compounds in enhancing or diminishing calcium fluxes in primary neuronal tissue culture. A test compound that increases calcium flux either (a) has little or no antagonist activity at the NMDA receptor and should not affect the potentiation of glycine activity through GlyT-1 transporter inhibition or (b), if marked increases are observed over comparison with GlyT-1 inhibitors that have little direct interaction with NMDA receptors, then the compound is a receptor agonist. In either of the above-described cases, the test confirms activity in treating or preventing schizophrenia, increasing cognition, or enhancing memory. In contrast, a test compound that decreases calcium flux has a net effect wherein receptor antagonist activity predominates over any activity the compound has in increasing glycine activity through inhibiting glycine transport. In this case, the test confirms activity in limiting or preventing the cell damage and cell death arising after stroke or other ischemia-inducing conditions, or in limiting or preventing the cell damage associated with neurodegenerative diseases.

The following examples further illustrate the present invention, but, of course, should not be construed as in any way limiting its scope.

EXAMPLE 1

This example sets forth methods and materials used for growing and transfecting QT-6 cells.

QT-6 cells were obtained from American Type Culture Collection (Accession No. ATCC CRL-1708). Complete QT-6 medium for growing QT-6 is Medium 199 (Sigma Chemical Company, St. Louis, Mo.; hereinafter "Sigma") supplemented to be 10% tryptose phosphate; 5% fetal bovine serum (Sigma); 1% penicillin-streptomycin (Sigma); and 1% sterile dimethylsulfoxide (DMSO; Sigma). Other solutions required for growing or transfecting QT-6 cells included:

DNA/DEAE Mix: 450 μl TBS, 450 μl DEAE Dextran (Sigma), and 100 μl of DNA (4 μg) in TE, where the DNA includes GlyT-1a, GlyT-1b, GlyT-1c, or GlyT-2, in a suitable expression vector. The DNA used was as defined below.

PBS: Standard phosphate buffered saline, pH 7.4 including 1 mM $CaCl_2$ and 1 mM $MgCl_2$ sterilized through 0.2μfilter.

TBS: One ml of Solution B, 10 ml of Solution A; brought to 100 ml with distilled $H_2O$; filter-sterilized and stored at 4° C.

TE: 0.01 M Tris, 0.001 M EDTA, pH 8.0.

DEAE dextran: Sigma, #D-9885. A stock solution was prepared consisting of 0.1% (1 mg/ml) of the DEAE dextran in TBS. The stock solution was filter sterilized and frozen in 1 ml aliquots.

Chloroquine: Sigma, #C-6628. A stock solution was prepared consisting of 100 mM chloroquine in $H_2O$. The stock solution was filter-sterilized and stored in 0.5 ml aliquots, frozen.

Solution A (10×):

| | |
|---|---|
| NaCl | 8.00 g |
| KCl | 0.38 g |
| $Na_2HPO_4$ | 0.20 g |
| Tris base | 3.00 g |

The solution was adjusted to pH 7.5 with HCl, brought to 100.0 ml with distilled $H_2O$, and filter-sterilized and stored at room temperature.

Solution B (10×):

| | |
|---|---|
| $CaCl_2 \cdot 2H_2O$ | 1.5 g |
| $MgCl_2 \cdot 6H_2O$ | 1.0 g |

The solution was brought to 100 ml with distilled $H_2O$, and filter-sterilized; the solution was then stored at room temperature.

HBSS: 150 mM NaCl, 20 mM HEPES, 1 mM $CaCl_2$, 10 mM glucose, 5 mM KCl, 1 mM $MgCl_2 \cdot H_2O$; adjusted with NaOH to pH 7.4.

Standard growth and passaging procedures used were as follows: Cells were grown in 225 ml flasks. For passaging, cells were washed twice with warm HBSS (5 ml each wash). Two ml of a 0.05% trypsin/EDTA solution was added, the culture was swirled, then the trypsin/EDTA solution was aspirated quickly. The culture was then incubated about 2 minutes (until cells lift off), then 10 ml of QT-6 media was added and the cells were further dislodged by swirling the flask and tapping its bottom. The cells were removed and transferred to a 15 ml conical tube, centrifuged at 1000 xg for 10 minutes, and resuspended in 10 ml of QT-6 medium. A sample was removed for counting, the cells were then diluted further to a concentration of $1 \times 10^5$ cells/ml using QT-6 medium, and 65 ml of the culture was added per 225 ml flask of passaged cells.

Transfection was accomplished using cDNAs prepared as follows:

The rat GlyT-2 (rGlyT-2) clone used contains the entire sequence of rGlyT-2 cloned into pBluescript SK +(Stratagene) as an Eco Rl - Hind lll fragment, as described in Liu et al., J. Biol. Chem. 268, 22802–22808 (1993). GlyT-2 was then subcloned into the pRc/RSV vector as follows: A PCR fragment corresponding to nucleotides 208 to 702 of the rGlyT-2 sequence [SEQ ID NO:4] was amplified by PCR using the oligonucleotide: 5' GGGGGAAGCT-TATGGATTGCAGTGCTCC 3' [SEQ ID NO:5] as the 5' primer and the oligonucleotide: 5' GGGGGGGTACCCAA-CACCACTGTGCTCTG 3' [SEQ ID NO:6] as the 3' primer. This created a Hind lll site immediately upstream of the translation start site. This fragment, which contained a Kpn l site at the 3' end, along with a Kpn 1 - Pvu ll fragment containing the remainder of the coding sequence of rGlyT-2, were cloned into pBluescript SK + previously digested with Hind lll and Sma l, in a three part ligation. A Hind lll - Xba 1 fragment from this clone was then subcloned into the pRc/RSV vector. The resulting construct contains nucleotides 208 to 2720 of the rGlyT-2 nucleic acid [SEQ ID NO:4] in the pRc/RSV expression vector.

The human GlyT-1a (hGlyT-1a) clone used contains the sequence of hGlyT-1a [SEQ ID NO:1] from nucleotide position 183 to 2108 cloned into the pRc/CMV vector (Invitrogen, San Diego, Calif.) as a Hind lll-Xba l fragment as described in Kim et al., *Mol. Pharmacol.*, 45, 608–617, 1994. This cDNA encoding GlyT-1 a actually contained the first 17 nucleotides (corresponding to the first 6 amino acids) of the GlyT-1a sequence from rat. To determine whether the sequence of human GlyT-1a was different in this region, the 5' region of hGlyT-1a from nucleotide 1 to 212 was obtained by rapid amplification of cDNA end using the 5' RACE system supplied by Gibco BRL (Gaithersburg, Md.). The gene specific primer: 5' CCACATTGTAGTAGATGCCG 3' [SEQ ID NO:7], corresponding to nucleotides 558 to 539 of the hGlyT-1a sequence [SEQ ID NO:1], was used to prime cDNA synthesis from human brain mRNA, and the gene specific primer: 5' GCAAACTGGCCGAAGGAGAGCTCC 3' [SEQ ID NO:8], corresponding to nucleotides 454 to 431 of the hGlyT-1a sequence [SEQ ID NO:1], was used for PCR amplification. Sequencing of this 5' region of GlyT-1 a confirmed that the first 17 nucleotides of coding sequence are identical in human and rat GlyT-1a.

The human GlyT-1b (hGlyT-1b) clone used contains the sequence of hGlyT-1b [SEQ ID NO:2] from nucleotide position 213 to 2274 cloned into the pRc/CMV vector as a Hind lll - Xba l fragment as described in Kim et al., supra.

The human GlyT-1c (hGlyT-1c) clone used contains the sequence of hGlyT-1c [SEQ ID NO:3] from nucleotide position 213 to 2336 cloned into the pRc/CMV vector (Invitrogen) as a Hind lll - Xba l fragment as described in Kim et al., supra. The Hind lll - Xba fragment of hGlyT-1c from this clone was then subcloned into the pRc/RSV vector. Transfection experiments were performed with GlyT-1c in both the pRc/RSV and pRc/CMV expression vectors.

The following four day procedure for the transfections was used:

On day 1, QT-6 cells were plated at a density of 1×10⁶ cells in 10 ml of complete QT-6 medium in 100 mm dishes.

On day 2, the medium was aspirated and the cells were washed with 10 ml of PBS followed by 10 ml of TBS. The TBS was aspirated, then 1 ml of the DEAE/DNA mix was added to the plate. The plate was swirled in the hood every 5 minutes. After 30 minutes, 8 ml of 80 $\mu$M chloroquine in QT-6 medium was added and the culture was incubated for 2.5 hours at 37° C. and 5% $CO_2$. The medium was then aspirated and the cells were washed two times with complete QT-6 medium, then 100 ml complete QT-6 medium was added and the cells were returned to the incubator.

On day 3, the cells were removed with trypsin/EDTA as described above, and plated into the wells of 96-well assay plates at approximately 2×10⁵ cells/well.

On day 4, glycine transport was assayed as described in Example 2.

EXAMPLE 2

This example illustrates a method for the measurement of glycine uptake by transfected cultured cells.

Transient GlyT-transfected cells or control ("mock") cells grown in accordance with Example 1 were washed three times with HEPES buffered saline (HBS). The mock cells were treated precisely as the GlyT-transfected cells except that the transfection procedure omitted any cDNA. The cells were incubated 10 minutes at 37° C., after which a solution was added containing 50 nM [$^3$H] glycine (17.5 Ci/mmol) and either (a) no potential competitor, (b) 10 mM nonradioactive glycine or (c) a concentration of a candidate drug. A range of concentrations of the candidate drug was used to generate data for calculating the concentration resulting in 50% of the effect (e.g., the $IC_{50}$s, which are the concentrations of drug inhibiting glycine uptake by 50%). The cells were then incubated another 20 minutes at 37° C., after which the cells were aspirated and washed three times with ice-cold HBS. The cells were harvested, scintillant was added to the cells, the cells were shaken for 30 minutes, and the radioactivity in the cells was counted using a scintillation counter. Data were compared between the cells contacted or not contacted by a candidate agent, and between cells having GlyT-1 activity versus cells having GlyT-2 activity, depending on the assay being conducted.

Positive control results are depicted in the bar graphs of FIGS. 1A and 1B, in which [$^3$H] glycine uptake is shown for mock, GlyT-1a, GlyT-1b, GlyT-1c, and GlyT-2 transformed cells. The results of the positive controls are presented as means ± SEM of a representative experiment performed in triplicate. All cell cultures transformed with any of the glycine transporters evidenced a significant increase in glycine transport activity as compared to non-transfected control cells.

EXAMPLE 3

This example illustrates the application of the method of Example 2, and the identification thereby of certain agents that regulate selectively the GlyT-1 or the GlyT-2 transporter, with respect to each other.

The agents recited below were tested for inhibition or enhancement of glycine transport in QT-6 cells that were transfected with pRc/CMV containing GlyT-1c [SEQ ID NO:3] or GlyT-2 [SEQ ID NO:4], and exhibited transient expression of GlyT-1c or GlyT-2, respectively, in accordance with the procedures of Examples 1 and 2 above.

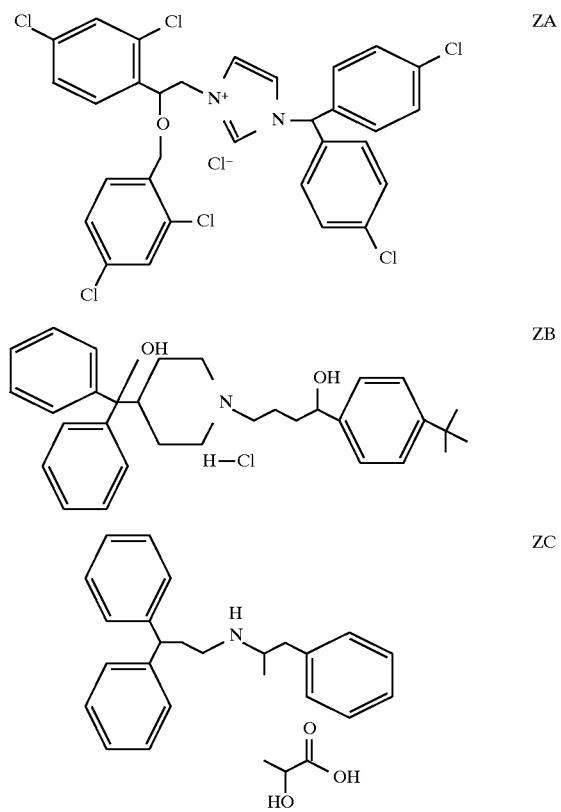

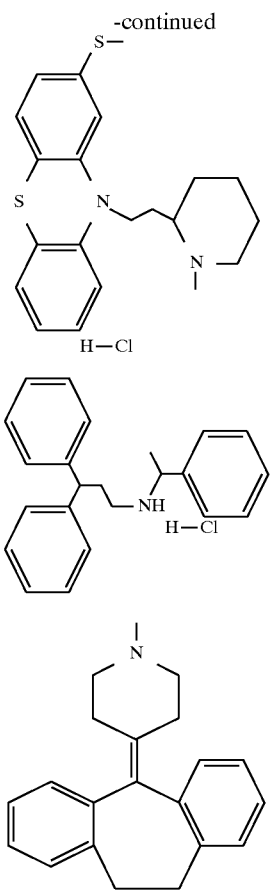

The data obtained with these compounds are as follows:

| Compound | Effect Via GlyT-1c* | Effect Via GlyT-2* |
|---|---|---|
| ZA | $pIC_{50} = 6.04$ | $pIC_{50} = 5.51$ |
| ZB | $pIC_{50} = 5.37$ | $pIC_{50} = 4.77$ |
| ZC | $pIC_{50} = 5.19$ | $pIC_{50} = 4.85$ |
| ZD | $pIC_{50} = 5.02$ | $pIC_{50} = 4.71$ |
| ZE | $pIC_{50} = 4.89$ | $pIC_{50} = 4.68$ |
| ZF | $pIC_{50} = 4.67$ | $pIC_{50} = 4.84$ |

*Transfected into QT-6 cells. The term "$pIC_{50}$" equals $-\log$ of $IC_{50}$, wherein $IC_{50}$ is the concentration of drug inhibiting glycine uptake by 50%.

Accordingly, compounds ZA, ZB, ZC, ZD, and ZE are each selective for GlyT-1 c relative to GlyT-2, whereas compound ZF shows the reverse selectivity.

EXAMPLE 4

This example illustrates binding assays to measure interaction of compounds with the glycine site on the NMDA receptor.

Direct binding of [$^3$H]glycine to the NMDA-glycine site was performed according to the method of Grimwood et al., *Molecular Pharmacology*, 41, 923–930 (1992); Yoneda et al., *J. Neurochem*, 62, 102–112 (1994).

Preparation of membranes for the binding test required application of a series of standard methods. Unless otherwise specified, tissues and homogenates were kept on ice and centrifugations were conducted at 4° C. Homogenizations were conducted with an effort to minimize resulting rise in tissue/homogenate temperature. The membrane preparation included the following steps:

1. Sacrifice and decapitate four rats; remove cortices and hippocampi.
2. Homogenize tissue in twenty volumes of 0.32 M sucrose/5 mM Tris-Acetate (pH 7.4) with 20 strokes of a glass/teflon homogenizer.
3. Centrifuge tissue at 1000×g, 10 minutes. Save supernatant. Resuspend pellet in small volume of buffer and homogenize again. Centrifuge the homogenized pellet and combine the supernatant with the previous supernatant.
4. Centrifuge the combined supernatants at 40,000×g, for 30 minutes. Discard the supernatant.
5. Resuspend the pellet in 20 volumes of 5 mM Tris-Acetate (pH 7.4). Stir the suspension on ice for one hour. Centrifuge the suspension at 40,000×g for 30 minutes. Discard the supernatant and freeze the pellet for at least 24 hours.
6. Resuspend the pellet from step 5 in Tris-Acetate buffer (5 mM, pH 7.4) containing 0.1% saponin (w/v; Sigma Chemical Co., St. Louis) to a protein concentration of 1 mg/ml. Leave on ice for 20 minutes. Centrifuge the suspension at 40,000×g for 30 minutes. Resuspend the pellet in saponin-free buffer and centrifuge again. Resuspend the pellet in Tris-Acetate buffer at a concentration of 10 mg/ml and freeze in aliquots.
7. On day three, remove an aliquot of membranes and thaw on ice. Dilute the suspension into 10 ml Tris-Acetate buffer and centrifuge at 40,000×g for 30 minutes. Repeat the wash step twice more for a total of 3 washes. Resuspend the final pellet at a concentration of 1 mg/ml in glycine-free Tris-Acetate buffer.

The binding test was performed in Eppendorf tubes containing approximately 150 μg of membrane protein and 50 nM [$^3$H]glycine in a volume of 0.5 ml. Non-specific binding was determined with 1 mM glycine. Drugs were dissolved in assay buffer (50 mM Tris-acetate, pH 7.4) or DMSO (final concentration of 0.1%). Membranes were incubated on ice for 30 minutes and bound radioligand was separated from free radioligand by filtration on Whatman GF/B glass fiber filters or by centrifugation (18,000×g, 20 min). Filters were washed three times quickly with ice-cold 5 mM Tris-acetate buffer. Filters were dried and placed in scintillation tubes and counted. Pellets were dissolved in deoxycholate/NaOH (0.1 N) solution overnight, neutralized and radioactivity was determined by scintillation counting.

A second binding test for the NMDA-glycine site used [$^3$H]dichlorokynurenic acid (DCKA) and membranes prepared as above. See, Yoneda et al., *J. Neurochem.*, 60, 634–645 (1993). The binding assay was performed as described for [$^3$H]glycine above except that [$^3$H]DCKA was used to label the glycine site. The final concentration of [$^3$H]DCKA was 10 nM, and the assay was performed for 10 minutes on ice.

A third binding test used for the NMDA-glycine site used indirect assessment of affinity of ligands for the site by measuring the binding of [$^3$H]MK-801 (dizocilpine; Palmer and Burns, *J. Neurochem.*, 62, 187–196 (1994)). Preparation of membranes for the test was the same as above. The binding assay allowed separate detection of antagonists and agonists.

Figure 2B:
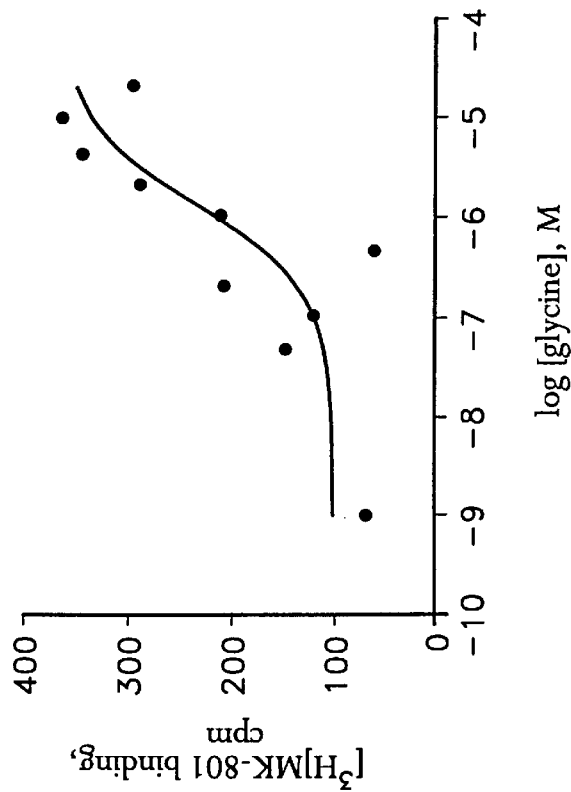
FIGS. 2A and 2B are graphs that respectively depict the attenuation of MK-801 binding by a glycine site antagonist (FIG. 2A) and the potentiation of MK-801 binding by a glycine site agonist (FIG. 2B).
Figure 2A:
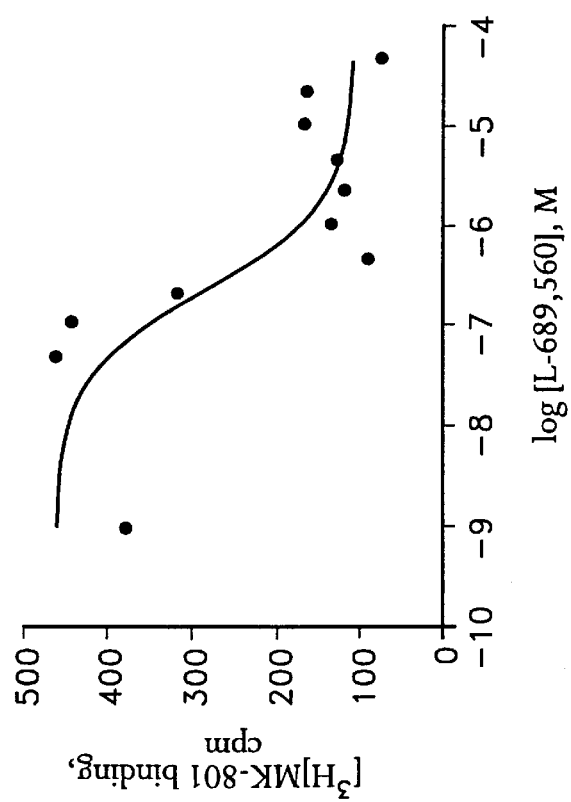

The third binding test was operated to identify antagonists as follows: 100 μg of membranes were added to wells of a 96-well plate, along with glutamate (10μM) and glycine (200 nM) and various concentrations of the ligand to be tested. The assay was started by the addition of 2.5 nM [$^3$H]MK-801 (23.9 Ci/mmol), which binds to the ion channel associated with NMDA receptors. The final volume of the assay was 200 μl. The assay was performed for 1 hour at room temperature. Bound radioactivity was separated from free by filtration, using a TOMTEC harvester. Antagonist activity was indicated by decreasing radioactivity associated with the NMDA receptor with increasing concentration of the tested ligand. Results of a positive control of this test are depicted in the graph of FIG. 2A, wherein the effect of varying concentrations of the glycine-site antagonist L-689,560 (represented as the log of the molar concentration of L-689,560 on the x-axis) is shown with respect to the resultant binding of [$^3$H]MK-801, indicated in counts per minute on the y-axis. The concentration of antagonist resulting in about a 50% effect was about $5 \times 10^{-7}$ M.

The third binding test was operated to identify agonists by performing the test as above, except that the concentration of glycine was 2 nM. Agonist activity was indicated by increasing radioactivity associated with the NMDA receptor with increasing concentration of the tested ligand. Results of a positive control of this test are depicted in the graph of FIG. 2B, wherein the effect of varying concentrations of glycine (x-axis, log of the molar concentration of glycine) is shown with respect to the resultant binding of [$^3$H]MK-801 in counts per minute (y-axis). The concentration of agonist (here, glycine itself) resulting in about a 50% effect was about $10^{-6}$ M.

EXAMPLE 5

This example illustrates a protocol for measuring calcium flux in primary neuronal cells, which is an indication of NMDA receptor activation.

The calcium flux measurement is performed in primary neuronal cell cultures, which are prepared from rat fetal cortices dissected from pregnant rats using standard procedures and techniques that require sterile dissecting equipment, a microscope and defined medium. The protocol used was adapted from Lu et al., *Proc. Nat'l. Acad. Sci. USA*, 88, 6289–6292 (1991).

Defined medium is prepared in advance in accordance with the following recipe:

| Components | Source (catalogue #) | Final Concentration |
|---|---|---|
| D-glucose | Sigma (G-7021) | 0.6% |
| transferrin | Sigma (T-2252) | 100 µg/ml |
| insulin | Sigma (I-5500) | 25 µg/ml |
| progesterone | Sigma (P-6149) | 20 nM |
| putrescine | Sigma (P-7505) | 60 µM |
| selenium | Sigma (S-5261) | 30 nM |
| pen-strep▲ | GIBCO (15070-014) | 0.5 U-0.5 µg/ml |
| L-glutamine* | GIBCO (25030-016) | 146 mg/l |
| MEM° | GIBCO (11095 or 11090) | 500 ml/l |
| F-12 | GIBCO (11765) | 500 ml/l |

▲pen-strep: 5,000 U/ml penicillin and 5,000 µg/ml steptomycin
*add only when MEM without L-glutamine is used
°with L-glutamine or without L-glutamine, respectively Before starting the dissection, tissue culture plates were treated with polylysine (100 µg/ml for at least 30 minutes at 37° C.) and washed with distilled water. Also, a metal tray containing two sets of sterile crude dissecting equipment (scissors and tweezers) and several sets of finer dissecting tools was autoclaved. A pair of scissors and tweezers were placed into a sterile beaker with 70% alcohol and brought to the dissecting table. A petri dish with cold phosphate buffered saline (PBS) was placed on ice next to the place of dissection.

A pregnant rat (E15 or 16 on arrival from Hilltop Lab Animals (Scottdale, Pa.), E17 or 18 at dissection) was placed in a $CO_2$/dry ice chamber until it was unconscious. The rat was removed, pinned to a backing, the area of dissection was swabbed with 70% alcohol, and skin was cut and removed from the area of interest. A second pair of scissors was used to cut through and remove the prenatal pups in their sacs. The string of sacs was placed into the cold PBS and transported to a sterile hood.

The prenatal pups were removed from the sacs and decapitated. The skulls were then removed and the brains were carefully dislodged and placed into a clean petri dish with cold PBS. At this point, it was necessary to proceed with a dissecting microscope. The brain was turned so that the cortices were contacting the plate and the tissue between the dissector and the cortex (stratum and other brain parts) was scooped out. The hippocampus and olfactory bulb were cut away from the cortex. Then the tissue was turned over and the meninges were removed with tweezers. The remaining tissue (cortex) was placed in a small petri dish with defined media.

The tissue was chopped with a scalpel and then triturated with a glass pipet that had been fire polished. The chopped, triturated tissue was then transferred to a sterile plastic tube and continued to be triturated with a glass pipet with a finer opening. Cells were counted in a suitable counting chamber. Cells were plated at roughly 200,000 cells/well in 500 µl of defined medium in 24-well plates. To inhibit glia growth, cultures were treated with 100 µM 5-flouro-2-deoxyuridine (FDUR, Sigma (F-0503)) or 50/µM uridine (Sigma (U-3003)) and 50 µM FDUR.

The cortical cultures for the standard calcium flux assay were grown in 24-well plates in the defined medium described above for 7 days and fed once with serum containing medium (10% heat inactivated fetal calf serum, 0.6% glucose in MEM) by exchanging half of the medium. Cultures were used after 12 days of incubation in vitro. The cultures were rinsed three times with HCSS (i.e. HEPES-buffered control salt solution, containing 120 mM NaCl, 5.4 mM KCl, 1.8 mM $CaCl_2$, 25 mM HEPES, and 15 mM glucose, in HPLC water and adjusted to pH 7.4 by NaOH, which was also made in HPLC water). In the third wash, the culture was incubated at 37° C. for 20 to 30 minutes.

Solutions containing $^{45}Ca^{++}$ ($1.5 \times 10^6$ dpm/ml) and drugs for testing or controls were prepared in HCSS. Immediately before the above $^{45}Ca^{++}$ solutions were added, cultures were washed twice with HCSS, and 250 µl of $^{45}Ca^{++}$ solution per well was added, one plate at a time. The cultures were incubated for 10 minutes at room temperature, rinsed three times with HCSS, and 1 ml scintillation liquid per well was added, followed by shaking for at least 15 minutes. Retained radioactivity was counted in a scintillation counter.

Figure 3:
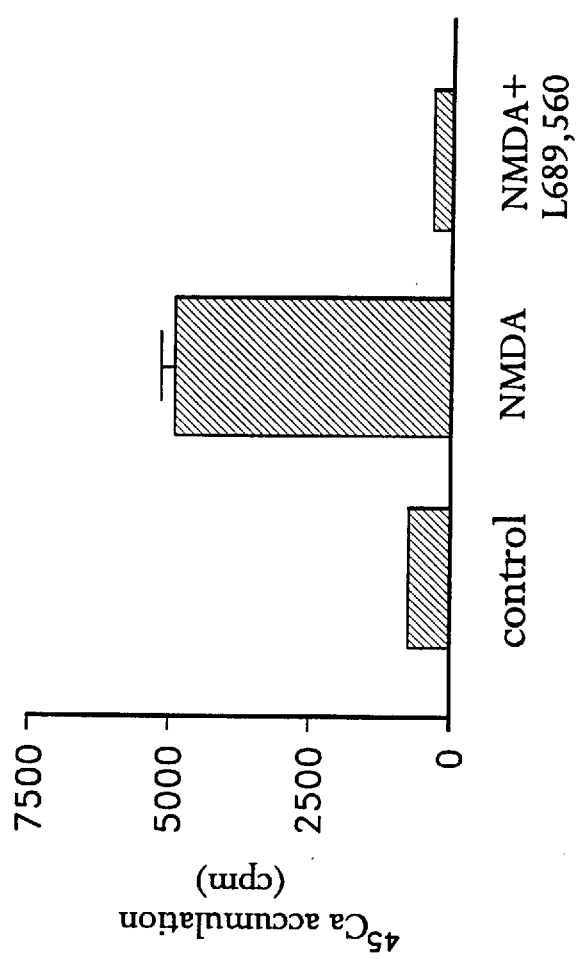
FIG. 3 is a bar graph that depicts NMDA receptor-mediated calcium uptake in primary neuronal cell cultures, and its blockade by the glycine site antagonist L-689,560.

Results of a standard calcium flux experiment are presented in FIG. 3. Primary neuronal cortical cell cultures were incubated with $^{45}Ca^{++}$ alone (control), in the presence of NMDA (500 µM), or NMDA (500 µM) and the antagonist L689,560 (50 µM), as described above. Data presented in the bar graph of FIG. 3 show the accumulation of $^{45}Ca^{++}$, and are the means ± SEM of a representative experiment (performed in triplicate) that was repeated with similar results. Accordingly, the results demonstrate that NMDA causes an increased accumulation of $^{45}Ca^{++}$, and that this effect is blocked by the glycine site antagonist L-689,560.

While this invention has been described with an emphasis upon preferred embodiments, it will be obvious to those of ordinary skill in the art that variations in the preferred compositions and methods may be used and that it is intended that the invention may be practiced otherwise than as specifically described herein. Accordingly, this invention includes all modifications encompassed within the spirit and scope of the invention as defined by the claims that follow the Sequence Listing.

We claim:

1. A method for the analysis of or screening for an agent that is an enhancer or inhibitor of glycine transport, comprising culturing separately a first and second avian cell, wherein the first and second avian cells are of the same strain and comprise an exogenous nucleic acid encoding a glycine transporter, contacting the first avian cell with the agent, and screening for the enhancement or inhibition of glycine transport into the first avian cell as compared to glycine transport into the second avian cell that was not contacted with the agent, wherein the glycine transport of the avian cell comprising the exogenous nucleic acid is greater than the glycine transport of the avian cell not comprising the exogenous nucleic acid.

2. The method of claim 1, wherein the glycine transporter is GlyT-1 or GlyT-2.

3. The method of claim 2, wherein the exogenous nucleic acid encodes GlyT-1.

4. The method of claim 3, wherein the exogenous nucleic acid comprises SEQ ID NO:1, SEQ ID NO:2, or SEQ ID NO:3.

5. The method of claim 1, wherein the first and second avian cell is a quail cell.

6. The method of claim 2, wherein the drug is an enhancer or inhibitor of GlyT-1 or GlyT-2, but not of both.

7. The method of claim 2, wherein the drug is an enhancer or inhibitor of GlyT-1 and GlyT-2.

8. The method of claim 1, wherein the agent is selected from those used to treat pain, spasticity, myoclonus, muscle spasm, muscle hyperactivity, epilepsy, stroke, head trauma, neuronal cell death, multiple sclerosis, spinal cord injury, dystonia, Alzheimer's disease, multi-infarct dementia, AIDS dementia, Parkinson's disease, Huntington's disease, amyotrophic lateral sclerosis, attention deficit disorder, organic brain syndromes, schizophrenia, and memory or cognitive disorders.

9. The method of claim 3, wherein the exogenous nucleic acid encodes GlyT-1a, GlyT-1b, or GlyT-1c.

10. The method of claim 9, wherein the exogenous nucleic acid encodes GlyT-1a.

11. The method of claim 10, wherein the exogenous nucleic acid comprises SEQ ID NO:1.

12. The method of claim 9, wherein the exogenous nucleic acid encodes GlyT-1b.

13. The method of claim 12, wherein the exogenous nucleic acid comprises SEQ ID NO:2.

14. The method of claim 9, wherein the exogenous nucleic acid encodes GlyT-1c.

15. The method of claim 14, wherein the exogenous nucleic acid comprises SEQ ID NO:3.

16. The method of claim 5, wherein the quail cell is a QT-6 cell.

* * * * *

SEQUENCE LISTING ( 1 ) GENERAL INFORMATION:

( i i i ) NUMBER OF SEQUENCES: 8

( 2 ) INFORMATION FOR SEQ ID NO:1:

( i ) SEQUENCE CHARACTERISTICS:
        ( A ) LENGTH: 2136 base pairs
        ( B ) TYPE: nucleic acid
        ( C ) STRANDEDNESS: double
        ( D ) TOPOLOGY: linear ( i i ) MOLECULE TYPE: cDNA ( x i ) SEQUENCE DESCRIPTION: SEQ ID NO:1:

```
AGAGCCTCGG  GAGGCTGATG  CAACTTTCCC  TTTAAGAAAG  CCACCTGGGC  GCACCGCGGT      60
GCGGACCCAG  CACGCCTGGG  CCGGGGGCTG  CAGCATGCTC  TTGAGATCTG  TGGCCTGAAA     120
GGCGCTGGAA  GCAGAGCCTG  TAAGTGTGGT  CCCCGTCACC  AGAGCCCCAA  CCCACCGCCG     180
CCATGGTAGG  AAAAGGTGCC  AAAGGGATGC  TGAATGGTGC  TGTGCCCAGC  GAGGCCACCA     240
AGAGGGACCA  GAACCTCAAA  CGGGGCAACT  GGGGCAACCA  GATCGAGTTT  GTACTGACGA     300
GCGTGGGCTA  TGCCGTGGGC  CTGGGCAATG  TCTGGCGCTT  CCCATACCTC  TGCTATCGCA     360
ACGGGGAGG   CGCCTTCATG  TTCCCCTACT  TCATCATGCT  CATCTTCTGC  GGGATCCCCC     420
TCTTCTTCAT  GGAGCTCTCC  TTCGGCCAGT  TTGCAAGCCA  GGGGTGCCTG  GGGGTCTGGA     480
GGATCAGCCC  CATGTTCAAA  GGAGTGGGCT  ATGGTATGAT  GGTGGTGTCC  ACCTACATCG     540
GCATCTACTA  CAATGTGGTC  ATCTGCATCG  CCTTCTACTA  CTTCTTCTCG  TCCATGACGC     600
ACGTGCTGCC  CTGGGCCTAC  TGCAATAACC  CCTGGAACAC  GCATGACTGC  GCCGGTGTAC     660
TGGACGCCTC  CAACCTCACC  AATGGCTCTC  GGCCAGCCGC  CTTGCCCAGC  AACCTCTCCC     720
ACCTGCTCAA  CCACAGCCTC  CAGAGGACCA  GCCCCAGCGA  GGAGTACTGG  AGGCTGTACG     780
TGCTGAAGCT  GTCAGATGAC  ATTGGGAACT  TGGGGAGGT   GCGGCTGCCC  CTCCTTGGCT     840
GCCTCGGTGT  CTCCTGGTTG  GTCGTCTTCC  TCTGCCTCAT  CCGAGGGGTC  AAGTCTTCAG     900
GGAAAGTGGT  GTACTTCACG  GCCACGTTCC  CCTACGTGGT  GCTGACCATT  CTGTTTGTCC     960
GCGGAGTGAC  CCTGGAGGGA  GCCTTTGACG  GCATCATGTA  CTACCTAACC  CCGCAGTGGG    1020
ACAAGATCCT  GGAGGCCAAG  GTGTGGGGTG  ATGCTGCCTC  CCAGATCTTC  TACTCACTGG    1080
CGTGCGCGTG  GGGAGGCCTC  ATCACCATGG  CTTCCTACAA  CAAGTTCCAC  AATAACTGTT    1140
ACCGGGACAG  TGTCATCATC  AGCATCACCA  ACTGTGCCAC  CAGCGTCTAT  GCTGGCTTCG    1200
TCATCTTCTC  CATCCTCGGC  TTCATGGCCA  ATCACCTGGG  CGTGGATGTG  TCCCGTGTGG    1260
CAGACCACGG  CCCTGGCCTG  GCCTTCGTGG  CTTACCCCGA  GGCCCTCACA  CTACTTCCCA    1320
TCTCCCCGCT  GTGGTCTCTG  CTCTTCTTCT  TCATGCTTAT  CCTGCTGGGG  CTGGGCACTC    1380
AGTTCTGCCT  CCTGGAGACG  CTGGTCACAG  CCATTGTGGA  TGAGGTGGGG  AATGAGTGGA    1440
TCCTGCAGAA  AAAGACCTAT  GTGACCTTGG  GCGTGGCTGT  GGCTGGCTTC  CTGCTGGGCA    1500
TCCCCCTCAC  CAGCCAGGCA  GGCATCTATT  GGCTGCTGCT  GATGGACAAC  TATGCGGCCA    1560
GCTTCTCCTT  GGTGGTCATC  TCCTGCATCA  TGTGTGTGGC  CATCATGTAC  ATCTACGGGC    1620
ACCGGAACTA  CTTCCAGGAC  ATCCAGATGA  TGCTGGGATT  CCCACCACCC  CTCTTCTTTC    1680
```

| | | | | | |
|---|---|---|---|---|---|
| AGATCTGCTG | GCGCTTCGTC | TCTCCCGCCA | TCATCTTCTT | TATTCTAGTT | TTCACTGTGA | 1740 |
| TCCAGTACCA | GCCGATCACC | TACAACCACT | ACCAGTACCC | AGGCTGGGCC | GTGGCCATTG | 1800 |
| GCTTCCTCAT | GGCTCTGTCC | TCCGTCCTCT | GCATCCCCCT | CTACGCCATG | TTCCGGCTCT | 1860 |
| GCCGCACAGA | CGGGGACACC | CTCCTCCAGC | GTTTGAAAAA | TGCCACAAAG | CCAAGCAGAG | 1920 |
| ACTGGGGCCC | TGCCCTCCTG | GAGCACCGGA | CAGGGCGCTA | CGCCCCACC | ATAGCCCCT | 1980 |
| CTCCTGAGGA | CGGCTTCGAG | GTCCAGTCAC | TGCACCCGGA | CAAGGCGCAG | ATCCCCATTG | 2040 |
| TGGGCAGTAA | TGGCTCCAGC | CGCCTCCAGG | ACTCCGGAT | ATAGCACAGC | TGCCAGGGGA | 2100 |
| GTGCCACCCC | ACCCGTGCTC | CACGAGAGAC | TGTGAG | | | 2136 |

( 2 ) INFORMATION FOR SEQ ID NO:2:

( i ) SEQUENCE CHARACTERISTICS:
    ( A ) LENGTH: 2202 base pairs
    ( B ) TYPE: nucleic acid
    ( C ) STRANDEDNESS: double
    ( D ) TOPOLOGY: linear ( i i ) MOLECULE TYPE: cDNA ( x i ) SEQUENCE DESCRIPTION: SEQ ID NO:2:

| | | | | | |
|---|---|---|---|---|---|
| GCCCACACAC | CCCACTCCAG | CTCCGGAGCA | CCCGTGCTGG | GCTGCATGGG | GACTGGCCGG | 60 |
| AGGGGCAGGG | CCAGGGGAGC | GGGTAGGCAG | AGCTTCGGGA | GGAGATGAGG | TGAAAGTAAT | 120 |
| TGACGCTGCC | CAGCCCGGCA | GTGGGAGAGG | CAGGGGATGC | GTCAGTGTCG | CGCTGGAGCT | 180 |
| GGCAGAGGTG | ATGAGCGGCG | GAGACACGCG | GGCTGCGAT | CGCTCGCCCC | AGGATGGCCG | 240 |
| CGGCTCATGG | ACCTGTGGCC | CCCTCTTCCC | CAGAACAGAA | TGGTGCTGTG | CCCAGCGAGG | 300 |
| CCACCAAGAG | GGACCAGAAC | CTCAAACGGG | GCAACTGGGG | CAACCAGATC | GAGTTTGTAC | 360 |
| TGACGAGCGT | GGGCTATGCC | GTGGGCCTGG | GCAATGTCTG | GCGCTTCCCA | TACCTCTGCT | 420 |
| ATCGCAACGG | GGGAGGCGCC | TTCATGTTCC | CCTACTTCAT | CATGCTCATC | TTCTGCGGGA | 480 |
| TCCCCCTCTT | CTTCATGGAG | CTCTCCTTCG | GCCAGTTTGC | AAGCCAGGGG | TGCCTGGGGG | 540 |
| TCTGGAGGAT | CAGCCCCATG | TTCAAAGGAG | TGGGCTATGG | TATGATGGTG | GTGTCCACCT | 600 |
| ACATCGGCAT | CTACTACAAT | GTGGTCATCT | GCATCGCCTT | CTACTACTTC | TTCTCGTCCA | 660 |
| TGACGCACGT | GCTGCCCTGG | GCCTACTGCA | ATAACCCCTG | GAACACGCAT | GACTGCGCCG | 720 |
| GTGTACTGGA | CGCCTCCAAC | CTCACCAATG | GCTCTCGGCC | AGCCGCCTTG | CCCAGCAACC | 780 |
| TCTCCCACCT | GCTCAACCAC | AGCCTCCAGA | GGACCAGCCC | CAGCGAGGAG | TACTGGAGGC | 840 |
| TGTACGTGCT | GAAGCTGTCA | GATGACATTG | GAACTTTGG | GGAGGTGCGG | CTGCCCCTCC | 900 |
| TTGGCTGCCT | CGGTGTCTCC | TGGTTGGTCG | TCTTCCTCTG | CCTCATCCGA | GGGGTCAAGT | 960 |
| CTTCAGGGAA | AGTGGTGTAC | TTCACGGCCA | CGTTCCCCTA | CGTGGTGCTG | ACCATTCTGT | 1020 |
| TTGTCCGCGG | AGTGACCCTG | GAGGGAGCCT | TTGACGGCAT | CATGTACTAC | CTAACCCCGC | 1080 |
| AGTGGGACAA | GATCCTGGAG | GCCAAGGTGT | GGGGTGATGC | TGCCTCCCAG | ATCTTCTACT | 1140 |
| CACTGGCGTG | CGCGTGGGA | GGCCTCATCA | CCATGGCTTC | CTACAACAAG | TTCCACAATA | 1200 |
| ACTGTTACCG | GGACAGTGTC | ATCATCAGCA | TCACCAACTG | TGCCACCAGC | GTCTATGCTG | 1260 |
| GCTTCGTCAT | CTTCTCCATC | CTCGGCTTCA | TGGCCAATCA | CCTGGGCGTG | GATGTGTCCC | 1320 |
| GTGTGGCAGA | CCACGGCCCT | GGCCTGGCCT | TCGTGGCTTA | CCCCGAGGCC | CTCACACTAC | 1380 |
| TTCCCATCTC | CCCGCTGTGG | TCTCTGCTCT | TCTTCTTCAT | GCTTATCCTG | CTGGGGCTGG | 1440 |
| GCACTCAGTT | CTGCCTCCTG | GAGACGCTGG | TCACAGCCAT | TGTGGATGAG | GTGGGGAATG | 1500 |

| | | | | | |
|---|---|---|---|---|---|
| AGTGGATCCT | GCAGAAAAAG | ACCTATGTGA | CCTTGGGCGT | GGCTGTGGCT | GGCTTCCTGC | 1560 |
| TGGGCATCCC | CCTCACCAGC | CAGGCAGGCA | TCTATTGGCT | GCTGCTGATG | GACAACTATG | 1620 |
| CGGCCAGCTT | CTCCTTGGTG | GTCATCTCCT | GCATCATGTG | TGTGGCCATC | ATGTACATCT | 1680 |
| ACGGGCACCG | GAACTACTTC | CAGGACATCC | AGATGATGCT | GGGATTCCCA | CCACCCTCT | 1740 |
| TCTTTCAGAT | CTGCTGGCGC | TTCGTCTCTC | CCGCCATCAT | CTTCTTTATT | CTAGTTTTCA | 1800 |
| CTGTGATCCA | GTACCAGCCG | ATCACCTACA | ACCACTACCA | GTACCCAGGC | TGGGCCGTGG | 1860 |
| CCATTGGCTT | CCTCATGGCT | CTGTCCTCCG | TCCTCTGCAT | CCCCCTCTAC | GCCATGTTCC | 1920 |
| GGCTCTGCCG | CACAGACGGG | GACACCCTCC | TCCAGCGTTT | GAAAAATGCC | ACAAAGCCAA | 1980 |
| GCAGAGACTG | GGGCCCTGCC | CTCCTGGAGC | ACCGGACAGG | GCGCTACGCC | CCCACCATAG | 2040 |
| CCCCCTCTCC | TGAGGACGGC | TTCGAGGTCC | AGTCACTGCA | CCCGGACAAG | GCGCAGATCC | 2100 |
| CCATTGTGGG | CAGTAATGGC | TCCAGCCGCC | TCCAGGACTC | CCGGATATAG | CACAGCTGCC | 2160 |
| AGGGGAGTGC | CACCCCACCC | GTGCTCCACG | AGAGACTGTG | AG | | 2202 |

( 2 ) INFORMATION FOR SEQ ID NO:3:

( i ) SEQUENCE CHARACTERISTICS:
 ( A ) LENGTH: 2364 base pairs
 ( B ) TYPE: nucleic acid
 ( C ) STRANDEDNESS: double
 ( D ) TOPOLOGY: linear ( i i ) MOLECULE TYPE: cDNA ( x i ) SEQUENCE DESCRIPTION: SEQ ID NO:3:

| | | | | | |
|---|---|---|---|---|---|
| GCCCACACAC | CCCACTCCAG | CTCCGGAGCA | CCCGTGCTGG | GCTGCATGGG | GACTGGCCGG | 60 |
| AGGGGCAGGG | CCAGGGGAGC | GGGTAGGCAG | AGCTTCGGGA | GGAGATGAGG | TGAAAGTAAT | 120 |
| TGACGCTGCC | CAGCCCGGCA | GTGGGAGAGG | CAGGGGATGC | GTCAGTGTCG | CGCTGGAGCT | 180 |
| GGCAGAGGTG | ATGAGCGGCG | GAGACACGCG | GGCTGCGAT | CGCTCGCCCC | AGGATGGCCG | 240 |
| CGGCTCATGG | ACCTGTGGCC | CCCTCTTCCC | CAGAACAGGT | GACGCTTCTC | CCTGTTCAGA | 300 |
| GATCCTTCTT | CCTGCCACCC | TTTTCTGGAG | CCACTCCCTC | TACTTCCCTA | GCAGAGTCTG | 360 |
| TCCTCAAAGT | CTGGCATGGG | GCCTACAACT | CTGGTCTCCT | TCCCCAACTC | ATGGCCCAGC | 420 |
| ACTCCCTAGC | CATGGCCCAG | AATGGTGCTG | TGCCCAGCGA | GGCCACCAAG | AGGGACCAGA | 480 |
| ACCTCAAACG | GGGCAACTGG | GCAACCAGA | TCGAGTTTGT | ACTGACGAGC | GTGGGCTATG | 540 |
| CCGTGGGCCT | GGGCAATGTC | TGGCGCTTCC | CATACCTCTG | CTATCGCAAC | GGGGAGGCG | 600 |
| CCTTCATGTT | CCCCTACTTC | ATCATGCTCA | TCTTCTGCGG | GATCCCCTC | TTCTTCATGG | 660 |
| AGCTCTCCTT | CGGCCAGTTT | GCAAGCCAGG | GGTGCCTGGG | GGTCTGGAGG | ATCAGCCCCA | 720 |
| TGTTCAAAGG | AGTGGGCTAT | GGTATGATGG | TGGTGTCCAC | CTACATCGGC | ATCTACTACA | 780 |
| ATGTGGTCAT | CTGCATCGCC | TTCTACTACT | CTTCTCGTC | CATGACGCAC | GTGCTGCCCT | 840 |
| GGGCCTACTG | CAATAACCCC | TGGAACACGC | ATGACTGCGC | CGGTGTACTG | GACGCCTCCA | 900 |
| ACCTCACCAA | TGGCTCTCGG | CCAGCCGCCT | TGCCCAGCAA | CCTCTCCCAC | CTGCTCAACC | 960 |
| ACAGCCTCCA | GAGGACCAGC | CCCAGCGAGG | AGTACTGGAG | GCTGTACGTG | CTGAAGCTGT | 1020 |
| CAGATGACAT | TGGGAACTTT | GGGGAGGTGC | GGCTGCCCCT | CCTTGGCTGC | CTCGGTGTCT | 1080 |
| CCTGGTTGGT | CGTCTTCCTC | TGCCTCATCC | GAGGGGTCAA | GTCTTCAGGG | AAAGTGGTGT | 1140 |
| ACTTCACGGC | CACGTTCCCC | TACGTGGTGC | TGACCATTCT | GTTTGTCCGC | GGAGTGACCC | 1200 |
| TGGAGGGAGC | CTTTGACGGC | ATCATGTACT | ACCTAACCCC | GCAGTGGGAC | AAGATCCTGG | 1260 |
| AGGCCAAGGT | GTGGGGTGAT | GCTGCCTCCC | AGATCTTCTA | CTCACTGGCG | TGCGCGTGGG | 1320 |

| | | | | | |
|---|---|---|---|---|---|
| GAGGCCTCAT | CACCATGGCT | TCCTACAACA | AGTTCCACAA | TAACTGTTAC | CGGGACAGTG | 1380
| TCATCATCAG | CATCACCAAC | TGTGCCACCA | GCGTCTATGC | TGGCTTCGTC | ATCTTCTCCA | 1440
| TCCTCGGCTT | CATGGCCAAT | CACCTGGGCG | TGGATGTGTC | CCGTGTGGCA | GACCACGGCC | 1500
| CTGGCCTGGC | CTTCGTGGCT | TACCCCGAGG | CCCTCACACT | ACTTCCCATC | TCCCCGCTGT | 1560
| GGTCTCTGCT | CTTCTTCTTC | ATGCTTATCC | TGCTGGGGCT | GGGCACTCAG | TTCTGCCTCC | 1620
| TGGAGACGCT | GGTCACAGCC | ATTGTGGATG | AGGTGGGGAA | TGAGTGGATC | CTGCAGAAAA | 1680
| AGACCTATGT | GACCTTGGGC | GTGGCTGTGG | CTGGCTTCCT | GCTGGGCATC | CCCCTCACCA | 1740
| GCCAGGCAGG | CATCTATTGG | CTGCTGCTGA | TGGACAACTA | TGCGGCCAGC | TTCTCCTTGG | 1800
| TGGTCATCTC | CTGCATCATG | TGTGTGGCCA | TCATGTACAT | CTACGGGCAC | CGGAACTACT | 1860
| TCCAGGACAT | CCAGATGATG | CTGGGATTCC | CACCACCCCT | CTTCTTTCAG | ATCTGCTGGC | 1920
| GCTTCGTCTC | TCCCGCCATC | ATCTTCTTTA | TTCTAGTTTT | CACTGTGATC | CAGTACCAGC | 1980
| CGATCACCTA | CAACCACTAC | CAGTACCCAG | CTGGGCCGT | GGCCATTGGC | TTCCTCATGG | 2040
| CTCTGTCCTC | CGTCCTCTGC | ATCCCCTCT | ACGCCATGTT | CCGGCTCTGC | CGCACAGACG | 2100
| GGGACACCCT | CCTCCAGCGT | TTGAAAAATG | CCACAAAGCC | AAGCAGAGAC | TGGGGCCCTG | 2160
| CCCTCCTGGA | GCACCGGACA | GGGCGCTACG | CCCCCACCAT | AGCCCCTCT | CCTGAGGACG | 2220
| GCTTCGAGGT | CCAGTCACTG | CACCCGGACA | AGGCGCAGAT | CCCCATTGTG | GGCAGTAATG | 2280
| GCTCCAGCCG | CCTCCAGGAC | TCCCGGATAT | AGCACAGCTG | CCAGGGGAGT | GCCACCCCAC | 2340
| CCGTGCTCCA | CGAGAGACTG | TGAG | | | | 2364

(2) INFORMATION FOR SEQ ID NO:4:

(i) SEQUENCE CHARACTERISTICS:
  (A) LENGTH: 2817 base pairs
  (B) TYPE: nucleic acid
  (C) STRANDEDNESS: double
  (D) TOPOLOGY: linear (ii) MOLECULE TYPE: cDNA (xi) SEQUENCE DESCRIPTION: SEQ ID NO:4:

| | | | | | |
|---|---|---|---|---|---|
| GAATTCGGCA | CGAGTCCGAA | TCCAAAGGGG | TAATGATTTA | TCAAACGTGT | ATTATCAGGA | 60
| AGATGTCAAA | CGAAGGGCAC | CTTGCTTCCC | ACTGACGCAA | ACCCGGCCTT | TCCTGGGGAG | 120
| ATATAGAAAG | CGCCTCTTGT | TCCAGGGCCA | AACCTAGACC | AGTAGCGGGG | TTTTACTCTA | 180
| CGGTTCAATC | TGTTGTCCGC | ATCAGACATG | GATTGCAGTG | CTCCCAAGGA | AATGAATAAA | 240
| CCACCAACCA | ACATCTTGGA | GGCAACGGTG | CCGGGCCACC | GGGATAGCCC | TCGAGCACCT | 300
| AGGACCAGCC | CTGAGCAGGA | TCTTCCTGCG | GCAGCCCCG | CGGCCGCTGT | CCAGCCGCCA | 360
| CGTGTGCCCA | GGTCGGCTTC | CACCGGCGCC | CAAACTTTCC | AGTCTGCGGA | TGCGAGAGCC | 420
| TGTGAGGCAC | AGCGGCCTGG | AGTAGGGTTT | TGTAAACTTA | GCAGCCCCA | GGCACAAGCG | 480
| ACCTCTGCGG | CCCTCCGGGA | CTTAAGCGAA | GGGCACAGCG | CACAGGCCAA | TCCCCTTCC | 540
| GGGGCCGCTG | GGGCTGGCAA | CGCTTTACAC | TGCAAGATTC | CAGCTCTGCG | TGGCCCGGAG | 600
| GAGGACGAGA | ACGTGAGTGT | GGCCAAGGGC | ACGCTGGAGC | ACAACAATAC | CCCACCCGTG | 660
| GGCTGGGTGA | ATATGAGCCA | GAGCACAGTG | GTGTTGGGTA | CCGATGGAAT | CGCGTCGGTG | 720
| CTCCCGGGCA | GCGTGGCCAC | CACTACCATT | CCGGAGGACG | AGCAAGGGGA | TGAGAATAAG | 780
| GCCAGAGGGA | ACTGGTCCAG | CAAACTGGAC | TTCATCCTGT | CCATGGTGGG | GTACGCAGTG | 840
| GGGCTGGGTA | ATGTTTGGAG | GTTTCCCTAC | CTGGCCTTCC | AGAACGGGGG | AGGTGCTTTC | 900

```
CTCATCCCTT  ACTTGATGAT  GCTGGCACTG  GCTGGCTTAC  CTATCTTCTT  CCTAGAGGTG    960
TCCCTGGGCC  AGTTTGCCAG  CCAGGGTCCT  GTGTCTGTGT  GGAAGGCCAT  CCCAGCTCTG   1020
CAGGGCTGTG  GCATTGCGAT  GCTCATCATC  TCCGTCCTCA  TAGCCATCTA  CTACAACGTC   1080
ATCATCTGCT  ACACGCTCTT  CTACCTGTTT  GCTTCTTTTG  TGTCTGTGCT  GCCCTGGGGA   1140
TCCTGCAACA  ACCCGTGGAA  CACACCAGAA  TGCAAAGACA  AAACCAAACT  TTTACTAGAT   1200
TCCTGTGTTA  TCGGTGACCA  TCCCAAGATA  CAGATCAAGA  ACTCTACTTT  CTGCATGACT   1260
GCCTATCCGA  ACTTGACCAT  GGTTAACTTC  ACCAGCCAGG  CCAATAAGAC  ATTTGTCAGC   1320
GGGAGTGAAG  AGTACTTCAA  GTACTTTGTG  CTGAAGATTT  CTGCAGGGAT  TGAATATCCT   1380
GGTGAGATCA  GGTGGCCCTT  GCCGTTCTGC  CTTTTCCTGG  CCTGGGTGAT  TGTATATGCA   1440
TCGCTGGCAA  AAGGAATTAA  GACATCAGGA  AAAGTGGTGT  ACTTCACAGC  CACCTTCCCT   1500
TATGTCGTCC  TGGTCATCCT  CCTCATTCGA  GGGGTCACCC  TGCCTGGAGC  TGGAGCCGGT   1560
ATCTGGTACT  TCATCACACC  TAAGTGGGAG  AAACTCACGG  ATGCCACGGT  GTGGAAGGAT   1620
GCAGCCACTC  AGATTTTCTT  CTCCCTGTCT  GCGGCCTGGG  GAGGGCTCAT  CACTCTTTCT   1680
TCTTACAACA  AATTCCATAA  CAACTGCTAC  AGGGACACGT  TAATTGTAAC  CTGCACCAAC   1740
AGTGCCACTA  GCATCTTCGC  TGGGTTTGTC  ATCTTCTCTG  TCATTGGCTT  CATGGCCAAC   1800
GAGCGCAAAG  TCAACATTGA  GAATGTGGCT  GACCAAGGGC  CAGGCATTGC  ATTTGTGGTT   1860
TACCCAGAAG  CCTTAACCAG  GCTGCCTCTC  TCTCCATTCT  GGGCCATCAT  CTTTTTCCTG   1920
ATGCTTCTCA  CGCTTGGACT  TGACACCATG  TTTGCTACCA  TCGAGACCAT  TGTGACCTCC   1980
ATCTCGGATG  AGTTTCCCAA  GTATCTGCGC  ACACACAAGC  CTGTGTTCAC  CCTGGGCTGC   2040
TGCATCTGCT  TCTTCATTAT  GGGCTTCCCA  ATGATCACAC  AGGGTGGAAT  CTACATGTTT   2100
CAGCTTGTGG  ACACCTATGC  TGCCTCCTAT  GCTCTTGTCA  TCATTGCCAT  ATTTGAGCTT   2160
GTTGGCATCT  CCTATGTGTA  CGGCTTGCAG  AGGTTCTGTG  AAGACATCGA  GATGATGATT   2220
GGATTCCAGC  CCAACATTTT  CTGGAAGGTC  TGCTGGGCGT  TTGTCACACC  GACCATTTTA   2280
ACGTTTATCC  TTTGCTTCAG  CTTCTATCAG  TGGGAGCCCA  TGACCTATGG  CTCCTACCGC   2340
TACCCTAACT  GGTCCATGGT  GCTTGGATGG  CTGATGCTCG  CCTGCTCCGT  GATCTGGATC   2400
CCGATTATGT  TCGTGATAAA  AATGTATCTG  GCTCCTGGGA  GATTATTGA   GAGGCTGAAG   2460
TTGGTATGCT  CGCCACAGCC  GGACTGGGGC  CCATTCTTAG  CTCAGCACCG  CGGGGAACGC   2520
TACAAGAATA  TGATCGACCC  CTTGGGAACC  TCGTCCCTGG  GACTCAAGCT  GCCAGTGAAG   2580
GATTTGGAAC  TGGGCACCCA  GTGCTAGTCC  AGTAGTGTGG  ATGGTCCCGT  ATTAATCCTG   2640
GGCTTCCTCT  CTGCCTCCCC  TCCACACTTT  CCCCAGATTT  ATTCCCAGTT  TTCTTCTTTC   2700
TCCCCACACC  TCGGTTCACA  GCTGTGCATG  AGAGTGTTCC  ATAGAAAAGT  AGGACCTAAC   2760
GTAGCATGCA  TTAAATCCAA  CTTCCTCTCA  CAAAAAAAAA  AAAAAAAAA   AAAGCTT      2817
```

( 2 ) INFORMATION FOR SEQ ID NO:5:

( i ) SEQUENCE CHARACTERISTICS:
        ( A ) LENGTH: 28 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:5:

```
GGGGGAAGCT  TATGGATTGC  AGTGCTCC                                            28
```

(2) INFORMATION FOR SEQ ID NO:6:

(i) SEQUENCE CHARACTERISTICS:
(A) LENGTH: 29 base pairs
(B) TYPE: nucleic acid
(C) STRANDEDNESS: single
(D) TOPOLOGY: linear (ii) MOLECULE TYPE: cDNA (xi) SEQUENCE DESCRIPTION: SEQ ID NO:6:

GGGGGGGTAC CCAACACCAC TGTGCTCTG 29

(2) INFORMATION FOR SEQ ID NO:7:

(i) SEQUENCE CHARACTERISTICS:
(A) LENGTH: 20 base pairs
(B) TYPE: nucleic acid
(C) STRANDEDNESS: single
(D) TOPOLOGY: linear (ii) MOLECULE TYPE: cDNA (xi) SEQUENCE DESCRIPTION: SEQ ID NO:7:

CCACATTGTA GTAGATGCCG 20

(2) INFORMATION FOR SEQ ID NO:8:

(i) SEQUENCE CHARACTERISTICS:
(A) LENGTH: 24 base pairs
(B) TYPE: nucleic acid
(C) STRANDEDNESS: single
(D) TOPOLOGY: linear (ii) MOLECULE TYPE: cDNA (xi) SEQUENCE DESCRIPTION: SEQ ID NO:8:

GCAAACTGGC CGAAGGAGAG CTCC 24